US012313635B2

(12) United States Patent
Cai

(10) Patent No.: US 12,313,635 B2
(45) Date of Patent: May 27, 2025

(54) BIOMARKER FOR THORACIC AORTIC ANEURYSM

(71) Applicant: THE REGENTS OF THE UNIVERSITY OF CALIFORNIA, Oakland, CA (US)

(72) Inventor: Hua Cai, Los Angeles, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 934 days.

(21) Appl. No.: 17/263,762

(22) PCT Filed: Jul. 26, 2019

(86) PCT No.: PCT/US2019/043761
§ 371 (c)(1),
(2) Date: Jan. 27, 2021

(87) PCT Pub. No.: WO2020/023922
PCT Pub. Date: Jan. 30, 2020

(65) Prior Publication Data
US 2021/0302438 A1    Sep. 30, 2021

Related U.S. Application Data

(60) Provisional application No. 62/711,348, filed on Jul. 27, 2018.

(51) Int. Cl.
*G01N 33/68* (2006.01)
*A61K 31/519* (2006.01)
*A61P 9/00* (2006.01)

(52) U.S. Cl.
CPC ....... *G01N 33/6893* (2013.01); *A61K 31/519* (2013.01); *A61P 9/00* (2018.01); *G01N 2800/329* (2013.01); *G01N 2800/52* (2013.01)

(58) Field of Classification Search
CPC ......... G01N 33/6893; G01N 2800/329; G01N 2800/52; A61K 31/519; A61P 9/00
See application file for complete search history.

(56) References Cited

U.S. PATENT DOCUMENTS

| 10,047,386 B2 | 8/2018 | Cai |
| 2002/0052374 A1 | 5/2002 | Rabelink et al. |
| 2007/0032533 A1 | 2/2007 | Garvey et al. |
| 2008/0175924 A1 | 7/2008 | Clelland et al. |
| 2010/0260747 A1 | 10/2010 | Schiffmann et al. |
| 2016/0346323 A1 | 12/2016 | Roth et al. |
| 2018/0073012 A1 | 3/2018 | Liu et al. |

FOREIGN PATENT DOCUMENTS

| WO | WO2009048884 A1 | 4/2009 | |
| WO | WO2010080452 A2 | 7/2010 | |
| WO | WO-2013055954 A1 * | 4/2013 | ............. C12Q 1/008 |
| WO | WO2017153023 A1 | 9/2017 | |

OTHER PUBLICATIONS

Mayo Clinic, (Wayback Machine, Feb. 14, 2018, < https://www.mayoclinic.org/diseases-conditions/aortic-aneurysm/symptoms-causes/syc-20369472>) (Year: 2018).*
Gao et al. Role of Uncoupled Endothelial Nitric Oxide Synthase in Abdominal Aortic Aneurysm Formation (Hypertension, 59: 158-166). (Year: 2012).*
Sselbacher, Eric, Thoracic and abdominal aortic aneurysms, Circulation. Feb. 15, 2005;111(6):816-28. doi: 10.1161/01.CIR.0000154569.08857.7A.
Extended European Search Report mailed Mar. 31, 2022 in corresponding EPO Application 19840602.7.
Brandes, Ralph P., Stay in Shape with BH4, Hypertension, May 29, 2018; 72:61-62. https://doi.org/10.1161/HYPERTENSIONAHA.118.11295.
Aortic Aneurysm. Mayo clinic.Mar. 9, 2018. [Retrieved Sep. 17, 2019] https://www.mayoclinic.org/diseases-conditions/aortic-aneurysm/symptoms-causes/syc-20369472.
Chalupsky, Karel., et al., "Intrinsic eNOS dysfunction causes vascular remodeling and abdominal aortic aneurysm", Mar. 2006, FASEB Journal, 20: A1161.
Crabtree, Mark J., et al., "Dihydrofolate reductase protects endothelial nitric oxide synthase from uncoupling in tetrahydrobiopterin deficiency", Mar. 2011, Free Radical Biology & Medicine, 50(2011): 1639-1646.
Galley, H.F., et al., "Circulating tetrahydrobiopterin concentrations in patients with septic shock", 2001, British Journal of Anaesthesia, 86(4): 578-80.
Gao, Ling, et al., "Role of uncoupled endothelial nitric oxide synthase in abdominal aortic aneurysm formation: treatment with folic acid", Nov. 14, 2011, Hypertension, 59(1): 158-66.
Kaneko, Y.S. et al., "Determination of tetrahydrobiopterin in murine locus coeruleus by HPLC with fluorescence detection", Aug. 2001, Brain Research Protocols, 8(1): 25-31.

(Continued)

*Primary Examiner* — Matthew P Coughlin
*Assistant Examiner* — Meghan C Heasley
(74) *Attorney, Agent, or Firm* — Karen S. Canady; canady + lortz LLP

(57) ABSTRACT

A method for detecting thoracic aortic aneurysm (TAA) or predisposition to TAA in a subject comprises measuring the amount of tetrahydrobiopterin ($H_4B$) present in the test sample; and comparing a measured amount of HUB to a standard amount of $H_4B$. A decreased amount of $H_4B$ present in the test sample compared to the standard is indicative of TAA or predisposition to TAA. The method can further comprise identifying a candidate for further testing or monitoring for TAA, such as by ultrasound or by repeated testing for $H_4B$ after one or more designated intervals. The method can also further comprise prescribing treatment for TAA to the subject, such as with folic acid therapy, and/or DHFR therapy, including gene therapy, and other therapies effective for recoupling eNOS and/or therapies targeting uncoupled eNOS. Methods are also described for monitoring the efficacy of treatment of TAA, and for evaluating the severity of TAA or risk of TAA.

16 Claims, 11 Drawing Sheets

(56) References Cited

OTHER PUBLICATIONS

Liao, Ming-fang, et al., "Role of nitric oxide and inducible nitric oxide synthase in human abdominal aortic aneurysms: a preliminary study", 2006, Chinese Medical Journal, 119(4): 312-318.

Schmidt, Tim S., et al., "Mechanisms for the role of tetrahydrobiopterin in endothelial function and vascular disease", 2007, Clinical Science, 113: 47-63.

Ueda, Seiji, et al., "Tetrahydrobiopterin Restores Endothelial Function in Long-Term Smokers", 1999, Journal of the American College of Cardiology, 35(1): 71-5.

Xiong, Wanfen, et al., "Inhibition of reactive oxygen species attenuates aneurysm formation in a murine model", Jan. 2009, Atherosclerosis, 202(1): 128-134.

Kuhlencordt et al., "Accelerated Atherosclerosis, Aortic Anurysm Formation, and Ischemic Heart Disease in Apolipoprotein E/Endothelial Nitric Oxide Synthase Double-Knockout Mice," Circulation, pp. 448-454, published 2001.

Stroes et al., "Folic Acid Reverts Dysfunction of Endothelial Nitric Oxide Synthase," Circulation Research, pp. 1129-1134, published Jun. 9, 2000.

Pimiento et al., "Endothelial Nitric Oxide Synthase Stimulates Aneurysm Growth in Aged Mice", J Vasc Res., vol. 45, pp. 251-258, published Jan. 10, 2008.

Fekkes et al., "Quantitation of total biopterin and tetrahydrobiopterin in plasma", Clinical Biochemistry, vol. 40, pp. 411-413, published online Jan. 5, 2007.

Galloway et al., "Serum Biopterin as a Marker of Immune Activation in the Spontaneously Diabetic BB rat", Pteridines, vol. 9, nol. 4, pp. 222-228, published 1998.

Moat et al., "Folic acid reverse endothelial dysfunction induced by inhibition of tetrahydrobiopterin biosynthesis", European Journal of Pharmacology, vol. 530, pp. 250-258, published 2006.

Shinozaki et al., "Coronary Endothelial Dysfunction in the Insulin-Resistant State Is Linked to Abnormal Pteridine Metabolism and Vascular Oxidative Stress" JACC, vol. 38, No. 7, pp. 1821-1828, published Dec. 2001.

WebMD (Aortic Aneurysm: Abdominal and Thoracic), published Oct. 1, 2010, retrieved from http://web.archive.org/web/20101001083211/http://www.webmd.com/heart-dise-ase/tc/aortic-aneurysm-overview (2 pages).

International Search Report for PCT/US19/43761 (WO2020/023922 Published Jan. 30, 2020).

\* cited by examiner

BIOMARKER FOR THORACIC AORTIC ANEURYSM

ACKNOWLEDGEMENT OF GOVERNMENT SUPPORT

This invention was made with government support under Grant Number HL077440, awarded by the National Institutes of Health. The government has certain rights in the invention.

TECHNICAL FIELD OF THE INVENTION

The present invention relates generally to a novel biomarker for thoracic aortic aneurysm and methods of using this biomarker for the diagnosis, risk detection, and monitoring of disease progression and response to treatment for aneurysm.

BACKGROUND OF THE INVENTION

Thoracic aortic aneurysm (TAA) is a prevalent human disease that affects 4.2% of the general population (Booher A M et al. Am Heart J. 2011). Despite surgical corrections, there have not been effective oral treatment or biomarkers for early detection, nor for monitoring of treatment efficacy and recidivism post-surgery.

There remains a need for biomarkers for TAA. In particular, there remains a need for biomarkers that can be used for screening, detecting and monitoring of TAA, as well as identifying those predisposed to developing TAA.

SUMMARY OF THE INVENTION

The invention provides a method for detecting thoracic aortic aneurysm (TAA) or predisposition to TAA in a subject. In some embodiments, the method comprises (a) measuring the amount of tetrahydrobiopterin ($H_4B$) present in the test sample; and (b) comparing a measured amount of $H_4B$ present in the test sample to a standard amount of $H_4B$. In some embodiments, the method comprises (a) contacting a test sample from the subject with an assay device capable of measuring the amount of tetrahydrobiopterin ($H_4B$) present in the test sample; and (b) comparing a measured amount of $H_4B$ present in the test sample to a standard amount of $H_4B$. In a typical embodiment of the invention, the sample comprises serum, plasma or whole blood. A decreased amount of $H_4B$ present in the test sample compared to the standard is indicative of TAA or predisposition to TAA. In some embodiments, a statistically significant decrease in the amount of $H_4B$ present in the test sample compared to the standard is indicative of TAA or predisposition to TAA. In other embodiments, the decrease in $H_4B$ is at least about a 10% decrease compared to the standard, or at least a 20%, 30%, 40%, 50% or 60%, 70%, 80% or 90% decrease. Smaller decreases are generally indicative of a predisposition to TAA, while larger decreases are more likely to indicate the presence of TAA.

Accordingly, the method can further comprise identifying a subject as a candidate for further testing or monitoring for TAA, such as by ultrasound or by repeated testing for $H_4B$ after one or more designated intervals. The method can also further comprise prescribing treatment for TAA to the subject whose $H_4B$ is decreased compared to the standard. Examples of the treatment comprise folic acid therapy, and/or DHFR (dihydrofolate reductase) therapy, including gene therapy.

Also provided is a method for monitoring the efficacy of treatment of TAA in a subject. In one embodiment, the method comprises (a) measuring the amount of $H_4B$ present in a first test sample from the subject obtained at a first time point; (b) measuring the amount of $H_4B$ present in a second test sample from the subject obtained at a second time point; and (c) comparing the measured amount of $H_4B$ present in the first and second test samples. In one embodiment, the method comprises (a) contacting a first test sample from the subject obtained at a first time point with an assay device capable of measuring the amount of $H_4B$ present in the test sample; (b) contacting a second test sample from the subject obtained at a second time point with an assay device capable of measuring the amount of $H_4B$ present in the test sample; and (c) comparing the measured amount of $H_4B$ present in the first and second test samples.

Treatment is administered to the subject prior to the second time point, and an increased amount of $H_4B$ present in the second test sample compared to the first test sample is indicative of effective treatment of TAA. This method can be initiated at the onset of treatment, or after a treatment plan is already underway. In some embodiments, a statistically significant increase in the amount of $H_4B$ present in the second sample compared to the first sample is indicative of effective treatment of TAA. In other embodiments, the increase in $H_4B$ is at least about a 10% increase compared to the first sample, or at least a 20%, 30%, 40%, 50% or 60%, 70%, 80%, 90%, 100%, 150%, 200% or greater increase. The method optionally further comprises prescribing a modified treatment for TAA to the subject whose $H_4B$ is decreased or increased compared to the first sample or compared to a standard.

The invention additionally provides a method for evaluating the severity of thoracic aortic aneurysm (TAA) or risk of TAA in a subject. In one embodiment, the method comprises (a) optionally, contacting a test sample from the subject with an assay device capable of measuring the amount of $H_4B$ present in the test sample; (b) measuring the amount of $H_4B$ present in the test sample; and (c) comparing the measured amount of $H_4B$ present in the test sample to a measured amount of $H_4B$ present in a standard. The extent of decrease in the amount of $H_4B$ present in the test sample compared to the standard is indicative of the severity or risk of TAA in the subject. In some embodiments, a statistically significant decrease in the amount of $H_4B$ present in the test sample compared to the standard is indicative of TAA or predisposition to TAA. In other embodiments, the decrease in $H_4B$ is at least about a 10% decrease compared to the standard, or at least a 20%, 30%, 40%, 50% or 60%, 70%, 80% or 90% decrease. Smaller decreases are generally indicative of a predisposition to, or a milder case of TAA, while larger decreases are more likely to indicate the presence of TAA, or a more severe case of TAA. Depending on the amount of $H_4B$ present in the test sample, the subject may be monitored or treated as described herein.

In a typical embodiment, the assay device comprises a high performance liquid chromatography (HPLC) column, or an immunoassay kit, such as an enzyme-linked immunosorbent assay (ELISA) kit, a chemiluminescence assay kit, or other conventional assay kit. Accordingly, the invention further provides a kit comprising reagents and/or an assay device for use in detection of $H_4B$.

DETAILED DESCRIPTION OF THE INVENTION

Figure 1:
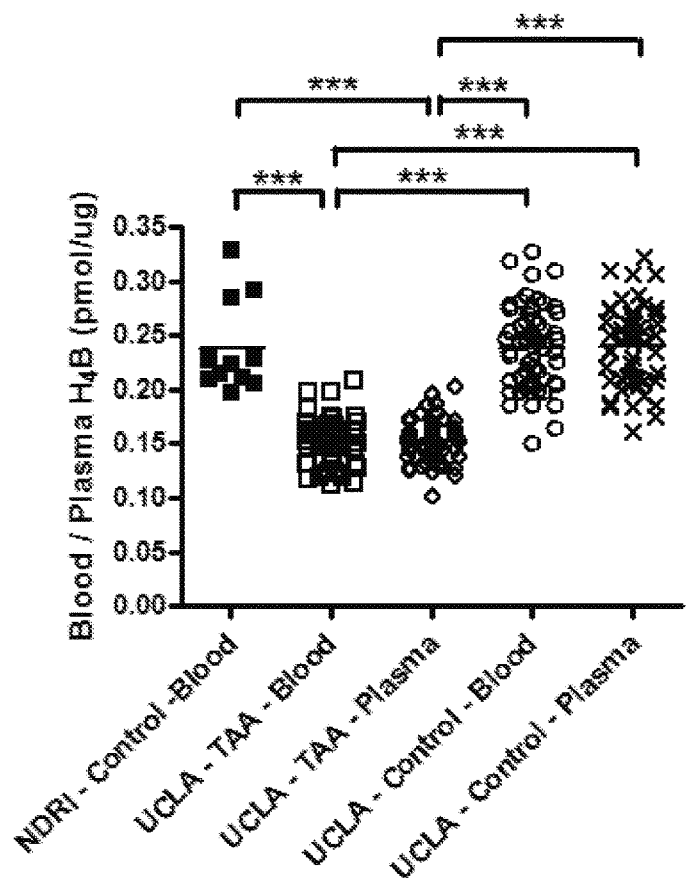
FIG. 1. Reduced levels of tetrahydrobiopterin ($H_4B$) can be used as a marker of TAA formation. A marked reduction of the circulating biomarker levels was found in TAA patients.

Described herein is the unexpected discovery that plasma levels of tetrahydrobiopterin (H$_4$B) can be utilized as a novel biomarker for thoracic aortic aneurysm (TAA), and that TAA formation can be abrogated with folic acid (FA) treatment. This discovery was surprising, given the apparent genetic determination of TAA and its association with congenital conditions, such as bicuspid aortic valve, Marfan syndrome, and Loeys-Dietz syndrome.

As described in U.S. Patent Publication No. 20140308686, published Oct. 16, 2014, circulating tetrahydrobiopterin (H$_4$B) can accurately predict its tissue levels, which are directly involved in the pathogenesis of abdominal aortic aneurysm (AAA). Based on extensive data from several novel and classical animal models and human patients, H$_4$B can be used as a biomarker for AAA. Traditionally, TAA is considered to be more genetically determined. Nonetheless, the present data surprisingly suggest that the genetic deficiencies can feed into a similar mechanistic pathway recently identified for AAA. Using two different models of AAA, namely angiotensin II infused hph-1 and apoE null mice, the prior studies demonstrate that plasma levels of H$_4$B correlate well with tissue H$_4$B levels, both of which were decreased in AAA and were restored by folic acid treatment.

Oral administration of folic acid leads to recoupling of eNOS and consequent reduction in oxidative stress and improvement in nitric oxide bioavailability, which in turn prevents vascular remodeling that precedes TAA. This results from folic acid upregulation of the eNOS cofactor salvage enzyme dihydrofolate reductase (DHFR). Thus, subjects identified via H$_4$B testing in accordance with the invention can be treated with folic acid or other therapies that promote DHFR, such as DHFR gene therapy. This early detection can reduce or eliminate the need for surgical repair and the risk of rupture.

Definitions

All scientific and technical terms used in this application have meanings commonly used in the art unless otherwise specified. As used in this application, the following words or phrases have the meanings specified.

As used herein, an "assay device" refers to an analytic instrument or apparatus customarily used to analyze, measure and/or detect the presence of a chemical substance. A typical example of such an instrument is a high performance liquid chromatography (HPLC) column. Other chromatography instruments can be used, as well as an immunoassay, chemiluminescence assay, or other conventional detection assay. A typical example of an immunoassay is an ELISA.

As is understood by those skilled in the art, a sample obtained from a subject may be brought into contact with an analytic instrument either directly, or after first being brought into contact with a solvent or other preparatory medium.

As used herein, a "control" sample is typically one obtained from one or more normal, healthy subjects, or where appropriate, from the same subject but at a time when the subject was known to be in a healthy condition. Also suitable as a control for comparison is an accepted normal level of the referenced analyte, referred to herein as a "standard".

As used herein, "pharmaceutically acceptable carrier" or "excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Compositions comprising such carriers are formulated by well-known methods (see, for example, *Remington's Pharmaceutical Sciences,* 18th edition, A. Gennaro, ed., Mack Publishing Co., Easton, PA, 1990).

As used herein, "a" or "an" means at least one, unless clearly indicated otherwise.

As used herein, to "prevent" or "protect against" a condition or disease means to hinder, reduce or delay the onset or progression of the condition or disease.

Methods

The invention provides a method for detecting thoracic aortic aneurysm (TAA) or predisposition to TAA in a subject. In some embodiments, the method comprises (a) measuring the amount of tetrahydrobiopterin ($H_4B$) present in the test sample; and (b) comparing a measured amount of $H_4B$ present in the test sample to a standard amount of $H_4B$. In some embodiments, the method comprises (a) contacting a test sample from the subject with an assay device capable of measuring the amount of tetrahydrobiopterin ($H_4B$) present in the test sample; and (b) comparing a measured amount of $H_4B$ present in the test sample to a standard amount of $H_4B$. In some embodiments, the method comprises detecting a decrease in the amount of $H_4B$ present in the test sample compared to a standard, control, or reference value. In a typical embodiment of the invention, the sample comprises serum, plasma or whole blood. A decreased amount of $H_4B$ present in the test sample compared to the standard is indicative of TAA or predisposition to TAA. The method can further comprise prescribing treatment for TAA to the subject whose $H_4B$ is decreased compared to the standard. Examples of the treatment comprise folic acid therapy, and/or dihydrofolate reductase (DHFR)-targeting therapies, including gene therapies, and any other pharmacological or other therapies effective in improving DHFR function, which will result in improved $H_4B$ levels and prevention, delay or amelioration of TAA. Likewise, treatment can comprise other countermeasures directed at recoupling eNOS and/or therapies targeting uncoupled eNOS.

In some embodiments, a statistically significant decrease in the amount of $H_4B$ present in the test sample compared to the standard is indicative of TAA or predisposition to TAA. Differences in circulating $H_4B$ levels in the range of 0.1 to 0.4 pmol/µg can be detected in humans with or without TAA. In some embodiments, a decrease in $H_4B$ levels to about 0.20-0.15 pmol/µg is indicative of TAA, and levels below ~0.15-0.10 pmol/µg are indicative of severe TAA. In other embodiments, the decrease in $H_4B$ is at least about a 10% decrease compared to the standard, or at least a 20%, 30%, 40%, 50% or 60%, 70%, 80% or 90% decrease. Smaller decreases, such as to the range of about 0.20 pmol/µg, are generally indicative of a predisposition to TAA, while larger decreases, such as to less than about 0.15 pmol/µg, are more likely to indicate the presence of TAA. The amount of circulating $H_4B$ correlates with the size of the aneurysm.

In some embodiments, the standard amount of $H_4B$ used for reference is adopted from a level accepted by those skilled in the art as normal for healthy subjects free of TAA this would vary depending on age and gender. In other embodiments, the standard used for comparison in the method is a sample obtained from normal, healthy control subjects. In yet other embodiments, the standard used for comparison is a test sample taken previously from the same subject at a time when the subject was known to be free of disease. Additional useful sources of reference levels for comparison include aneurismal and adjacent tissues routinely collected during open TAA repair surgery, as well as blood, plasma, serum, or other body fluid samples collected prior to surgery. Thus, in some embodiments, the level of $H_4B$ in the test sample obtained from the subject is compared to both normal standard levels of $H_4B$ and known abnormal levels obtained from TAA samples.

Optionally, the method can further comprise identifying a subject as a candidate for further testing or monitoring for TAA, such as by ultrasound or by repeated testing for $H_4B$ after one or more designated intervals. For example, subjects with more severe cases may be monitored monthly, while those with mild cases may be monitored every three months. The treating physician will be able to adjust this schedule based on the needs and risks for an individual patient. Thus, the method can be repeated and the measured amount of $H_4B$ can be compared either to the standard or to a previous measurement from the same subject. Initial monitoring may comprise repeat testing for $H_4B$, and the subject can be referred for treatment and/or ultrasound evaluation after $H_4B$ testing indicates significant progression toward TAA. Measuring changes in $H_4B$ levels can detect TAA before it can be detected via ultrasound. Early detection of TAA allows for less aggressive treatment and avoidance of surgery. For example, if a subject exhibits an initial 5-10% reduction, is later observed to show a 15% reduction after a follow-up period, the subject needs to be monitored more frequently than those who do not show any reduction or a steady level of small reduction of <10% over time.

Also provided is a method for monitoring the efficacy of treatment of TAA in a subject. In one embodiment, the method comprises (a) measuring the amount of $H_4B$ present in a first test sample from the subject obtained at a first time point; (b) measuring the amount of $H_4B$ present in a second test sample from the subject obtained at a second time point; and (c) comparing the measured amount of $H_4B$ present in the first and second test samples. In one embodiment, the method comprises (a) contacting a first test sample from the subject obtained at a first time point with an assay device capable of measuring the amount of $H_4B$ present in the test sample; (b) contacting a second test sample from the subject obtained at a second time point with an assay device capable of measuring the amount of $H_4B$ present in the test sample; and (c) comparing the measured amount of $H_4B$ present in the first and second test samples. In one embodiment, the method comprises detecting an insufficient increase in the $H_4B$ present in a second sample compared to a first, pre-treatment or early-treatment sample. Preferably, identical or nearly identical assay device and conditions are used for obtaining the first and second test samples.

Treatment is administered to the subject prior to the second time point, and an increased amount of $H_4B$ present in the second test sample compared to the first test sample is indicative of effective treatment of TAA. This method can be initiated at the onset of treatment, or after a treatment plan is already underway. In some embodiments, a statistically significant increase in the amount of $H_4B$ present in the second sample compared to the first sample is indicative of effective treatment of TAA. In other embodiments, the increase in $H_4B$ is at least about a 10% increase compared to the first sample, or at least a 20%, 30%, 40%, 50% or 60%, 70%, 80%, 90%, 100%, 150%, 200% or greater increase. The method optionally further comprises prescribing a modified treatment for TAA to the subject whose $H_4B$ is decreased or increased compared to the first sample or compared to a standard. For example, the treatment can be modified by increasing or decreasing the amount of folic acid or other therapeutic agent administered to the subject.

The invention additionally provides a method for evaluating the severity of thoracic aortic aneurysm (TAA) or risk of TAA in a subject. In one embodiment, the method comprises (a) optionally, contacting a test sample from the subject with an assay device capable of measuring the amount of $H_4B$ present in the test sample: (b) measuring the amount of $H_4B$ present in the test sample; and (c) comparing the measured amount of $H_4B$ present in the test sample to a measured amount of $H_4B$ present in a standard. The extent of decrease in the amount of $H_4B$ present in the test sample compared to the standard is indicative of the severity or risk of TAA in the subject. In some embodiments, a statistically significant decrease in the amount of $H_4B$ present in the test sample compared to the standard is indicative of TAA or predisposition to TAA. In other embodiments, the decrease in $H_4B$ is at least about a 10% decrease compared to the standard, or at least a 20%, 30%, 40%, 50% or 60%, 70%, 80% or 90% decrease. Smaller decreases are generally indicative of a predisposition to, or a milder case of TAA, while larger decreases are more likely to indicate the presence of TAA, or a more severe case of TAA. Depending on the amount of $H_4B$ present in the test sample, the subject may be monitored or treated as described herein.

In a typical embodiment of the invention, the sample comprises serum, plasma, or whole blood, but it can be any body fluid. In a typical example, 2 ml of whole blood is drawn from the subject, although less than about 0.5 ml can be sufficient. The sample can be collected in a variety of conditions, including with or without spin down at the time of collection. Samples can be processed using, for example, a variety of collection tubes including supplement free, EDTA-containing, Heparin containing, and other conditions known in the art. Likewise, samples can be collected and stored under a variety of conditions, including, for example, by snap-freezing in liquid nitrogen and then transferred to −70° C. or −80° C.; or freezing at −70° C. or −80° C. and storing samples from there.

Assay Devices and Kits

In a typical embodiment, the assay device comprises a high performance liquid chromatography (HPLC) column, or an immunoassay kit, such as an enzyme-linked immunosorbent assay (ELISA) kit, a chemiluminescence assay kit, or other conventional assay kit. In a typical embodiment, the HPLC is equipped with a fluorescent or electrochemical detector and a C-18 column.

For use in the methods described herein, kits are also within the scope of the invention. Such kits can comprise a carrier, package or container that is compartmentalized to receive one or more containers such as vials, tubes, and the like, each of the container(s) comprising one of the separate elements to be used in the method. For example, the container(s) can comprise one or more reagents for use in detecting $H_4B$ that is, optionally, detectably labeled. The kit can also include one or more containers for a reporter-means, such as a biotin-binding protein, e.g., avidin or streptavidin, bound to a detectable label, e.g., an enzymatic, florescent, or radioisotope label for use in detecting $H_4B$.

The kit of the invention will typically comprise the container described above and one or more other containers comprising materials desirable from a commercial and user standpoint, including buffers, diluents, filters, needles, syringes, and package inserts with instructions for use. In addition, a label can be provided on the container to indicate that the composition is used for a specific application, and can also indicate directions for use. Directions and or other information can also be included on an insert which is included with the kit.

Administration and Dosage

The compositions are administered in any suitable manner, often with pharmaceutically acceptable carriers, excipients, or in the form of a pharmaceutically acceptable salt. Suitable methods of administering treatment in the context of the present invention to a subject are available, and, although more than one route can be used to administer a particular composition, a particular route can often provide a more immediate and more effective reaction than another route.

The dose administered to a patient, in the context of the present invention, should be sufficient to effect a beneficial therapeutic response in the patient over time, or to inhibit disease progression. Thus, the composition is administered to a subject in an amount sufficient to elicit an effective response and/or to alleviate, reduce, cure or at least partially arrest symptoms and/or complications from the disease. An amount adequate to accomplish this is defined as a "therapeutically effective dose." In general, for pharmaceutical compositions comprising folic acid, the amount present in a dose ranges from about 1 to about 100 mg per kg of body weight of the subject, and higher. Representative amounts include, but are not limited to, 1, 5, 15, 30, 100 or higher mg/kg body weight. Suitable amounts will vary with the size of the patient, but will typically range from about 1-20 mg/tablet or 0.1 mL to about 5 mL.

Routes and frequency of administration of the therapeutic compositions disclosed herein, as well as dosage, will vary from individual to individual, and may be readily established using standard techniques. In general, the pharmaceutical compositions may be administered orally, or by injection (e.g., intracutaneous, intramuscular, intravenous or subcutaneous), intranasally (e.g., by aspiration). Typically, at least 1 to 10 doses may be administered over a 52 week period. Preferably, 6 doses are administered, at intervals of 1 month, and additional supplements may be given periodically thereafter. Alternate protocols may be appropriate for individual patients. In one embodiment, 2 or more oral supplements are administered 10 days apart. When treating with folic acid, it is typically best taken daily, particularly for patients with TAA. Less frequent administration can be sufficient for subjects at risk of TAA, who have not yet developed TAA.

In general, an appropriate dosage and treatment regimen provides the active agent(s) in an amount sufficient to provide therapeutic and/or prophylactic benefit. Such a response can be monitored by establishing an improved clinical outcome in treated patients as compared to non-treated patients, including by monitoring biomarker values during the periods of the treatment.

Treatment includes prophylaxis and therapy. Prophylaxis or therapy can be accomplished by a single administration at a single time point or multiple time points to a single or multiple sites. In some embodiments, the administration is oral. Administration can also be nearly simultaneous to multiple sites. Patients or subjects include mammals, such as human, bovine, equine, canine, feline, porcine, and ovine animals. The subject is preferably a human.

Exemplary Embodiments

Embodiment 1: A method for detecting thoracic aortic aneurysm (TAA) or predisposition to TAA in a subject, the method comprising: (a) measuring the amount of tetrahydrobiopterin ($H_4B$) present in the test sample; and (b) comparing a measured amount of $H_4B$ present in the test sample to a standard amount of $H_4B$; wherein a decreased amount of $H_4B$ present in the test sample compared to the standard is indicative of TAA or predisposition to TAA.

Embodiment 2: The method of embodiment 1, wherein the measuring comprises contacting the test sample with an assay device.

Embodiment 3: The method of embodiment 2, wherein the assay device comprises an immunoassay kit.

Embodiment 4: The method of embodiment 2, wherein the assay device comprises a high performance liquid chromatography (HPLC) column.

Embodiment 5: The method of embodiment 1, wherein a 20% decrease in the amount of $H_4B$ present in the test sample compared to the standard is indicative of TAA or predisposition to TAA.

Embodiment 6: The method of embodiment 1, wherein a 50% decrease in the amount of $H_4B$ present in the test sample compared to the standard is indicative of TAA or predisposition to TAA.

Embodiment 7: The method of embodiment 1, further comprising prescribing treatment for TAA to the subject whose $H_4B$ is decreased compared to the standard.

Embodiment 8: The method of embodiment 7, wherein the treatment comprises folic acid therapy.

Embodiment 9: The method of embodiment 8, wherein the folic acid therapy comprises oral administration of folic acid.

Embodiment 1: The method of embodiment 1, wherein the sample comprises plasma, serum or whole blood.

Embodiment 10: A method for monitoring the efficacy of treatment of TAA in a subject, the method comprising: (a) contacting a first test sample from the subject obtained at a first time point with an assay device capable of measuring the amount of tetrahydrobiopterin ($H_4B$) present in the test sample; (b) contacting a second test sample from the subject obtained at a second time point with an assay device capable of measuring the amount of tetrahydrobiopterin ($H_4B$) present in the test sample; (c) comparing the measured amount of tetrahydrobiopterin ($H_4B$) present in the first and second test samples; wherein treatment is administered to the subject prior to the second time point, and wherein an increased amount of $H_4B$ present in the second test sample compared to the first test sample is indicative of effective treatment of TAA.

Embodiment 11: The method of embodiment 10, wherein the assay device comprises a high performance liquid chromatography (HPLC) column.

Embodiment 12: The method of embodiment 10, wherein the assay device comprises an immunoassay kit.

Embodiment 13: The method of embodiment 10, wherein a 20% increase in the amount of $H_4B$ present in the second test sample compared to the first test sample is indicative of effective treatment of TAA.

Embodiment 14: The method of embodiment 10, wherein the sample comprises plasma, serum or whole blood.

Embodiment 15: The method of embodiment 10, further comprising prescribing a modified treatment for TAA to the subject whose $H_4B$ is decreased or increased compared to the standard.

Embodiment 16: A method for evaluating the severity of thoracic aortic aneurysm (TAA) or risk of TAA in a subject, the method comprising: (a) contacting a test sample from the subject with an assay device capable of measuring the amount of tetrahydrobiopterin ($H_4B$) present in the test sample; and (b) measuring the amount of tetrahydrobiopterin ($H_4B$) present in the test sample; (c) comparing the measured amount of $H_4B$ present in the test sample to a measured amount of $H_4B$ present in a standard; wherein the extent of decrease in the amount of $H_4B$ present in the test sample compared to the standard is indicative of the severity or risk of TAA in the subject.

Embodiment 17: The method of embodiment 16, wherein the assay device comprises a high performance liquid chromatography (HPLC) column.

Embodiment 18: The method of embodiment 16, wherein the assay device comprises an immunoassay kit.

Embodiment 19: The method of embodiment 16, wherein the sample comprises serum or whole blood.

Embodiment 20: The method of embodiment 16, further comprising prescribing treatment for TAA to the subject whose $H_4B$ is decreased compared to the standard.

Embodiment 21: The method of embodiment 16, wherein a 50% decrease in the amount of $H_4B$ present in the test sample compared to the standard is indicative of severe TAA.

Embodiment 22: A method for treating thoracic aortic aneurysm (TAA) or predisposition to TAA in a subject, the method comprising: (a) measuring, in a test sample of serum, plasma or whole blood from the subject, the amount of tetrahydrobiopterin ($H_4B$) present in the test sample; wherein a 20% decrease is detected in the measured amount of $H_4B$ present in the test sample relative to a standard amount of $H_4B$; and (b) treating the subject with oral administration of folic acid therapy for TAA if a 20% decrease is detected in the measured amount of $H_4B$ present in the test sample relative to a standard amount of $H_4B$.

Embodiment 23: The method of embodiment 22, wherein the decrease is a 30% decrease in the amount of $H_4B$ present in the test sample compared to the standard.

Embodiment 24: The method of embodiment 22, wherein the decrease is a 40% decrease in the amount of $H_4B$ present in the test sample compared to the standard.

Embodiment 25: The method of embodiment 22, wherein the decrease is a 50% decrease in the amount of $H_4B$ present in the test sample compared to the standard.

EXAMPLES

The following examples are presented to illustrate the present invention and to assist one of ordinary skill in making and using the same. The examples are not intended in any way to otherwise limit the scope of the invention.

Example 1: Tetrahydrobiopterin as a Marker of TAA Formation

This Example demonstrates that reduced levels of tetrahydrobiopterin ($H_4B$) can be used as a marker of TAA formation. In a large cohort of TAA patients recruited at the UCLA Ronald Regan Medical Center, a marked reduction of the circulating biomarker levels was found in TAA patients (FIG. 1). Blood and plasma $H_4B$ levels were measured in control and thoracic aortic aneurysm (TAA) patients. Both blood and plasma $H_4B$ levels in TAA patients were markedly lower in TAA patients compared to the control groups (from both UCLA and NIH NDRI). These results were shown to be statistically significant ($p<0.001$) by One-way ANOVA.

Thus, despite distinct features and documented differential mechanistic insights of the two types of aneurysms, AAA and TAA, the data presented here suggest that the mechanisms underlying thoracic aortic aneurysm lie downstream of the genetic factors to allow the same biomarker to be applicable for use in detecting and treating both types of aneurysm.

Example 2: Prevention of Thoracic Aortic Aneurysm Formation Via Dietary Folic Acid This example demonstrates that folic acid (FA) administration can be used to treat and prevent TAA formation. This study examined whether eNOS uncoupling mediates formation of thoracic aortic aneurysm (TAA) and AAA in $Fbn1^{C1039G/+}$ Marfan Syndrome (MFS) mice, and whether and how countermeasures directed against TGFβ signaling and eNOS uncoupling could attenuate Marfan aneurysms. Briefly, $Fbn1^{C1039G/+}$ mice were treated with FA diet or TGFβ neutralizing antibody (anti-TGFβ). Diameters of aortic roots and abdominal aortas were measured using echocardiography, while aortic superoxide and nitric oxide (NO) levels were determined by electron spin resonance. Aortic and circulating levels of tetrahydrobiopterin ($H_4B$) were determined using HPLC. Protein expression of NOX4, and inactive/active forms of TGFβ, were assayed by Western blotting. The results show that FA diet markedly attenuated expansion of aortic roots and abdominal aortas in $Fbn1^{C1039G/+}$ mice, which was accompanied by upregulated $H_4B$ salvage enzyme dihydrofolate reductase (DHFR) expression and activity, restored tissue and circulating levels of $H_4B$, recoupling of eNOS and improved NO bioavailability. Circulating $H_4B$ levels were accurately predictive of tissue $H_4B$ bioavailability, and negatively associated with expansion of aortic roots. Therefore, circulating $H_4B$ levels serve as a novel biomarker for TAA development and response to treatment. The expression of mature/active TGFβ and its downstream effector NOX4 were upregulated in $Fbn1^{C1039G/+}$ mice, but attenuated by anti-TGFβ treatment in vivo to result in recoupling of eNOS and attenuated aneurysm formation. These data for the first time reveal that uncoupled eNOS represents a central mediator of TAA formation in $Fbn1^{C1039G/+}$ MFS mice, while FA diet or TGFβ antagonism abrogates aneurysm formation via recoupling of eNOS. These data also establish a novel Fbn1/TGFβ/NOX4/eNOS uncoupling axis in the development of Marfan aneurysms, targeting of which may facilitate development of novel therapeutics for the treatment of TAAs.

Aortic aneurysms are associated with significant morbidity and mortality, accounting for 1-2% of all deaths in industrialized countries[1], contributing to more than 16,450 deaths annually in the United States[2]. Aneurysmal disease in humans has strong hereditary influence, particularly for thoracic aortic aneurysm (TAA) compared to abdominal aortic aneurysm (AAA)[3]. Hereditary thoracic aortic aneurysm and dissection (HTAAD) includes Marfan syndrome (MFS), Loeys-Dietz syndrome (LDS), vascular Ehlers-Danlos syndrome (vEDS) and other HTAAD conditions[3-6]. Exploration of the hereditary roots of the diseases has identified cellular and molecular events such as uncontrolled release of TGFβ and activation of the TGFβ pathway in MFS. Dysregulation of TGFβ is believed to induce secretion of matrix-degrading enzymes such as MMPs, representing a common pathway for aneurysm formation[3].

It has been established that fibrillin-1 (FBN1) mutation is responsible for aneurysm formation in patients with MFS[8]. Fibrillin-1 is the principal constituent of 10-nm microfibrils and functions as a skeleton for the deposition of tropoelastin, providing both load-bearing and anchoring functions within the arterial wall[9]. Manifestations of MFS involve multiple organ systems including the aorta, heart and valves, skeleton, eye, lungs, and dura[10]. In 1955, Dr. McKusick first described cardiovascular features of MFS[1]. The primary cardiovascular abnormality is an aneurysm of the aortic root, which often extends into the proximal portion of the tubular ascending thoracic aorta to create pear-shaped aortic dilatation[3]. Aortic aneurysm and dissection are the most life-threatening MFS manifestations[4, 12].

The role of the TGFβ in TAA among different animal models is different or controversials[5, 12, 13]. MFS mice with non-dissecting TAA ($Fbn1^{C1039G/+}$ mice) developed aneurysm as a result of over-stimulation of TGFβ production and signaling by improper activity of the AT1R[5, 14]. Besides, noncanonical (smad-independent) TGFβ signaling is found to be a prominent driver of aortic disease in $Fbn1^{C1039G/+}$ mice[15]. However, MFS mice with a more severe phenotype ($Fbn1^{mgR/mgR}$ mice) demonstrated deleterious effects of TGF-β inhibition on TAA. It was reported that anti-TGFβ neutralizing antibody enhanced aortic rupture and aneurysm in both thoracic and abdominal regions in Ang II-infused C57BL/6J mice[16].

A critical role of oxidative stress has been demonstrated in the pathogenesis of AAA[17-22]. As to TAA, evidence indicates a correlation between oxidative stress and TAA in humans[23]. In situ production of ROS and expression of NADPH oxidase subunit p22phox were markedly increased in human TAA tissues, and the formation of aneurysms could be inhibited by Statins and AT1R blocker (ARB) via suppression of p22phox[23]. NOX4 expression was increased in the tunica media of human Marfan aorta, and was transcriptionally upregulated in VSMC[24]. Of note, $Fbn1^{C1039G/+}$-$NOX4^{-/-}$ double mutant mice displayed a reduction in fragmented elastic fibers in aortas, which was accompanied by an amelioration of the Marfan-associated enlargement of the aortic root[24]. In addition, NOX4 deletion in Marfan mice aggravated middle cerebral artery (MCA) wall thickening, accompanied by increased collagen deposition[25].

Recent work has established a direct causal role of uncoupled eNOS and endothelium-derived reactive oxygen species (ROS) in AAA formation in both novel and classical models of AAA including Ang II infused hph-1 mice and Ang I-infused apoE null mice[19-22]. Furthermore, recoupling of eNOS with oral administration of folic acid (FA) completely or largely attenuated AAA formation in these animals[21, 22]. Therefore, the hypotheses that eNOS uncoupling is induced by TGFβ-dependent initial increase in ROS production to result in aneurysm formation in Fbn1$^{C1039G/+}$ mice, and that targeting uncoupled eNOS with FA diet or TGFβ signaling with anti-TGFβ antibody is effective in preventing Marfan aneurysms via attenuation of NOX4 expression was tested. Fbn1$^{C1039G/+}$ mice were treated with FA diet or TGFβ neutralizing antibody (anti-TGFβ). Diameters of aortic roots and abdominal aortas were age-dependently increased in Fbn1$^{C1039G/+}$ mice, which were substantially attenuated by FA administration. This was associated with markedly increased tissue and circulating $H_4B$ levels, recoupling of eNOS and improved NO bioavailability. The circulating $H_4B$ levels correlated well with that of tissue levels and sizes of aortic roots, indicating a novel biomarker role of circulating $H_4B$ for TAA development and response to treatment. The expression and activity of endothelial DHFR were substantially upregulated in both Fbn1$^{+/+}$ and Fbn1$^{C1039G/+}$ mice, resulting in restored $H_4B$ levels. Of note, the baseline deficiency in $H_4B$ levels in Fbn1$^{C1039G/+}$ mice was due to reduced expression of GTPCHI in mice. The expression of mature TGFβ and its downstream effector NOX4 were elevated in Fbn1$^{C1039G/+}$ mice compared to Fbn1$^{+/+}$. In vivo treatment with anti-TGFβ abrogated NOX4 expression, recoupled eNOS and attenuated the expansion of aortic roots. Therefore, TGFβ/NOX4/eNOS uncoupling axis represents a novel molecular pathway of TAA formation in Fbn1$^{C1039G/+}$ mice, targeting of which may facilitate development of novel therapeutics for Marfan aneurysms and other types of TAA.

Materials and Methods

Chemical Reagents

Unless otherwise noted, all chemicals and reagents are purchased from Sigma-Aldrich in highest purity. Isoflurane was purchased from Piramal Healthcare.

Animals

Figure 2:
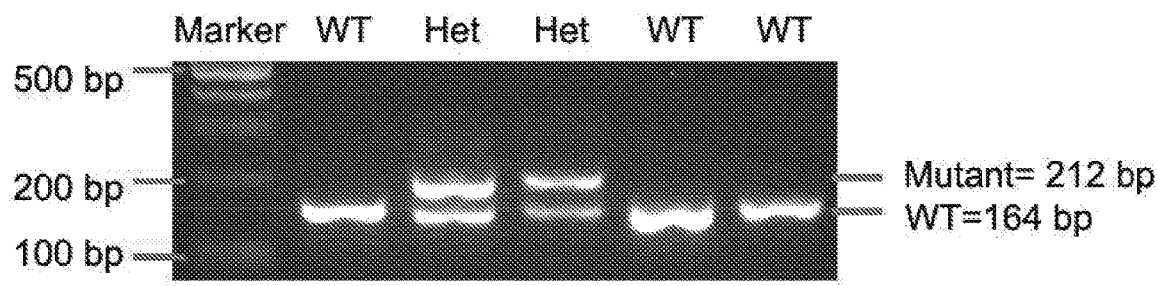
FIG. 2. The genotyping of Fbn1$^{C1039G/+}$ mice. WT: wild-type (164 bp, Fbn1$^{+/+}$), Het: Heterozygous (212 bp and 164 bp, Fbn1$^{C1039G/+}$).

All experimental procedures were approved by the Institutional Animal Care and Usage committee at the University of California, Los Angeles (UCLA). Original heterozygous Fbn1$^{C1039G/+}$ male animals were purchased from Jackson Labs (Bar Harbor, ME, Strain B6.129-Fbn1$^{tm1Hcd/J}$, stock #012885). Heterozygous mice develop proximal aortic aneurysms, mitral valve thickenings, pulmonary alveolar septation defects, mild thoracic kyphosis, and skeletal myopathy, but 90% reportedly live to one year of age. This strain was backcrossed to C57BL/6 for more than nine generations by the donating laboratory[14]. All pups were genotyped using PCR (FIG. 2) as per instructions by Jackson Labs.

Folic Acid Treatment

For animal groups treated with folic acid (FA), standard chow was replaced with in-house customized food tablets containing FA (15 mg/kg/day) that have been shown to recouple eNOS via restoration of dihydrofolate reductase (DHFR) function to improve tetrahydrobiopterin bioavailability[21, 22, 26]. FA treatment started at 4 weeks of age, and lasted through the entire study period of 8 weeks till harvest.

Ultrasound Imaging of Aortic Root and the Abdominal Aorta

Animals were anesthetized with isoflurane (~15%), and secured onto a temperature controlled table to maintain temperature at 37° C. Hair from the abdomen and the chest were removed with a hair removal cream (Nair). Preheated ultrasound transmission gel was applied to the chest (for the aortic root) or the abdomen (for the abdominal aorta). An ultrasound probe (Velvo 2100, echocardiograph, MS-400) was placed on the gel to visualize the aorta transversely. For the abdominal aorta, the aorta was first confirmed by the identification of pulsatile flow using Doppler measurements. Consistent localization of the image acquisition was insured by imaging the area immediately superior to the branch of the left renal artery. For the aortic root, the aorta that is immediately superior to the heart was imaged, and the aorta was confirmed by using Doppler measurements. All images were recorded and saved for later offline aortic dimension analysis.

Measurement of Superoxide Using Electron Spin Resonance (ESR)

Aortic superoxide was measured by ESR as previously described[19-22, 26-33]. Briefly, freshly isolated aortas were homogenized on icein lysis buffer containing 1:100 protease inhibitor cocktail, and centrifuged at 12,000 g for 15 min. Protein content of the supernatant was determined using a protein assay kit (Bio-Rad, #500-0113, #500-0114, #500-0115). Five µg of protein was mixed with ice-cold and nitrogen bubbled Krebs/HEPES buffer containing diethyldithiocarbamic acid (5 µmol/L), deferoxamine (25 µmol/L), and the superoxide specific spin trapmethoxycarbonyl-2,2, 5,5-tetramethylpyrrolidine (CMH, 500 µmol/L, Axxora, San Diego, CA, USA). The mixture was then loaded into a glass capillary (Kimble, Dover, OH, USA), and assayed using the ESR spectrometer (eScan, Bruker, Billerica, MA, USA) for superoxide production. A second measurement was taken with the addition ofPEG-SOD (100 U/mL) for the determination of background. For the assessment of eNOS uncoupling, a third measurement was made with the addition of L-NAME (100 µmol/L). ESR settings used were: Center field, 3480; Sweep width, 9 G; microwave frequency, 9.78 GHz; microwave power, 21.02 mW; modulation amplitude, 2.47 G; 512 points of resolution; receiver gain, 1000.

Measurement of Nitric Oxide (NO) Using Electron Spin Resonance

Aortic N O production was also measured using ESR as previous described[19-22, 26-29, 32-34]. Briefly, freshly isolated aortas were cut into 2 mm rings, and then incubated in freshly prepared NO specific spin trap $Fe^{2+}(DETC)_2$ (0.5 mmol/L) in nitrogen bubbled, modified Krebs/HEPES buffer (as described above) at 37° C. for 60 min, in the presence of calcium ionophore A23187 (10 µmol/L). The aortic rings were then snap frozen in liquid nitrogen and loaded into a finger Dewarfor measurement with ESR. The instrument settings were as the following: Center field, 3440; Sweep width, 100 G: microwave frequency, 9.796 GHz; microwave power 13.26 mW; modulation amplitude, 9.82 G; 512 points of resolution; and receiver gain 356.

Measurement of Tetrahydrobiopeterin ($H_4B$) Using HPLC

Aortic $H_4B$ and plasma $H_4B$ were measured using HPLC as previously described[19-22, 26, 27, 32, 33, 35-37]. For the aorta, freshly isolated aortas were lysed in $H_4B$ lysis buffer (0.1 M phosphoric acid, 1 mM EDTA, 10 mM dl-dithiothreitol) and then centrifuged at 12,000 g for 3 min at 4° C. in the dark. For plasma, equal volumes of plasma and $H_4B$ lysis buffer were mixed and incubated on ice for 20 min in the dark and then centrifuged at 12,000 g for 3 min at 4° C. in the dark. The supernatant for both the aorta and plasma was subjected to oxidation in acidic (0.2 M trichloroacetic acid with 2.5% 12 and 10% KI) and alkalytic solutions (0.1 M NaOH with 0.9% 12 and 1.5% KI). After centrifugation, 10 µl of the supernatant was injected into a HPLC system equipped with a fluorescent detector (SHIMADZU AMERICA INC, Carlsbad, CA, USA). Excitation and emission wavelengths of 350 nm and 450 nm were used to detect $H_4B$ and its oxidized species. $H_4B$ concentration was calculated as previously described[38, 39].

Western Blotting

Western blotting was performed following standard protocols, using 12.5% SDS/PAGE gel and nitrocellulose membranes. Primary antibodies and their dilutions used were: DHFR (1:500, Novus Biologicals, H00001719-MO1), β-actin (1:3000, Sigma-Aldrich, A2066), eNOS (1:2000, BD Transduction Laboratories, 610297), TGFβ (1:500, Abcam, ab92486), NOX4 (1:300, Novus Biologicals, NB110-58849SS), and GTPCH 1 (1:500, Abbiotec, 250680).

Determination of DHFR Activity Using HPLC

DHFR activity was measured from isolated EC or denuded aorticring lysates as previously described[19, 22, 26]. Briefly, lysates were incubated in a DHFR assay buffer (0.1 mol/L potassium phosphate dibasic, 1 mmol/L DTT, 0.5 mmol/L KCl, 1 mmol/L EDTA, and 20 mmol/L sodium ascorbate at pH 7.4) with NADPH (200 μmol/L) and the substrate dihydrofolate (50 μmol/L) at 37° C. for 20 min in the dark. The product of the reaction, tetrahydrofolate (THF), was measured using a HPLC system (SHIMADZU AMERICA INC, Carlsbad, CA, USA) with a C-18 column (Alltech, Deerfield, MA, USA) using water based mobile phase consisting of 7% acetonitrile and 5 mmol/L of potassium phosphate dibasic at pH 2.3. The signal was detected using a fluorescent detector at 295 nm excitation and 365 nm emission. The THF content was calculated against a standard curve prepared using THF solutions in assay buffer. Data are presented as nmol production of THF per min per mg protein.

In Vivo Treatment with Anti-TGFβ Antibody

Four weeks old heterozygous $Fbn1^{C1039G/+}$ male animals were treated with TGFβ neutralizing antibody (anti-TGFβ, clone 1D11, Bio X Cell) or isotype (IgG, clone MOPC21, Bio X Cell) as previously shown[40]. One mg anti-TGFβ or isotype reagents were injected intraperitoneally on the first day, and then 200 μg was injected intraperitoneally every the other day for the other 13 times. The ultrasound imaging of aortic root and the abdominal aorta were performed every week as described above. Aortic superoxide production and eNOS uncoupling activity were determined after 4 weeks injection as described above.

Statistical Analysis

All analyses were performed using the Graphpad Prism software. Comparison between 2 groups was performed using the student's t-test. Comparison among multiple groups was performed using the ANOVA, followed by the Newman-Keuls post-hoc test. Statistical significance was set at $p<0.05$. All grouped data are presented as Mean±SEM.

Results

Figure 3A:
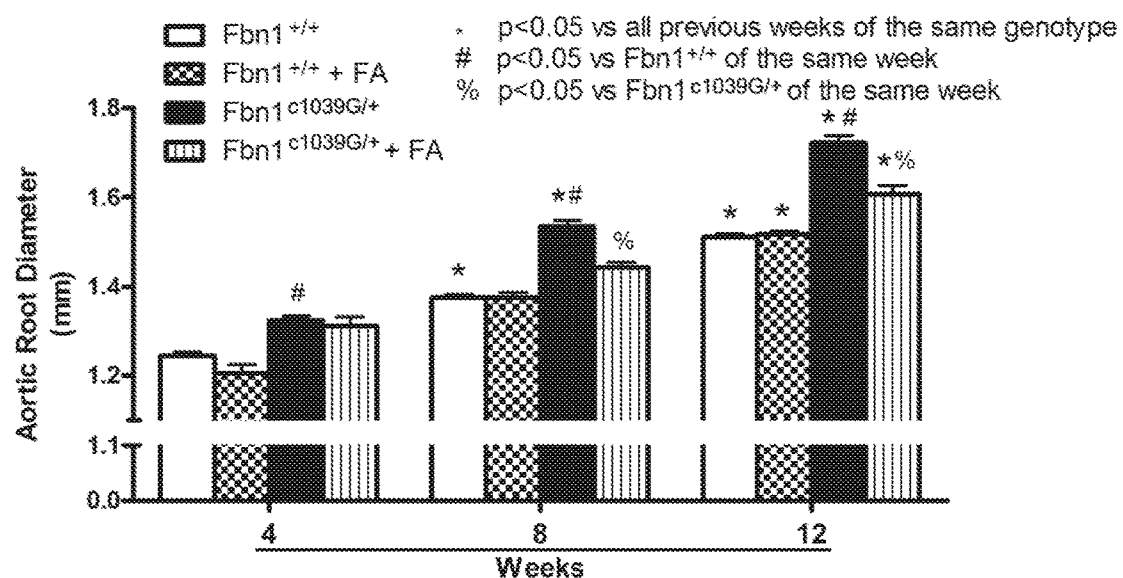
FIGS. 3A-3B. Recoupling of eNOS with folic acid diet abrogates expansion of aortic roots and abdominal aortas in Fbn1$^{C1039G/+}$ animals. Diameters of aortic roots (3A) and abdominal aortas (3B) were measured using echocardiography and found significantly increased in Fbn1C$^{C1039G/+}$ mice, which were substantially attenuated by recoupling of eNOS with folic acid diet. Data are presented as Mean±SEM, n=19-38.
Figure 3B:
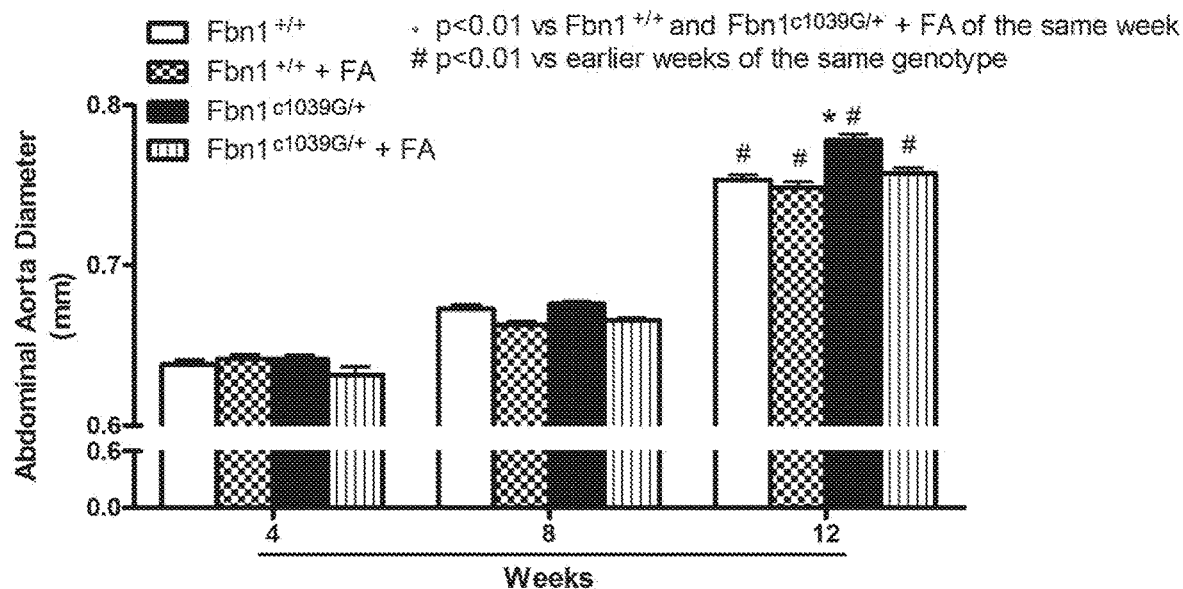

Recoupling of eNOS with oral administration of folic acid inhibited aortic root and abdominal aortic expansion in $Fbn1^{C1039G/+}$ mice Ultrasound images were taken to examine the size of the aortic roots and abdominal aortas in $Fbn1^{+/+}$ or $Fbn1^{C1039G/+}$ mice with or without FA treatment. $Fbn1^{C1039G/+}$ mice showed significant expansion of both the aortic roots and the abdominal aortas compared to $Fbn1^{+/+}$ (FIGS. 3A&3B). However, the aortic roots and abdominal aortas of the $Fbn1^{C1039G/+}$ mice treated with FA food were substantially smaller than that of $Fbn1^{C1039G/+}$ mice fed with chow diet. These results indicated that FA treatment might be an effective treatment approach to attenuate aneurysm formation in MFS.

Folic acid reduced superoxide production, improved NO bioavailability and recoupled eNOS in $Fbn1^{C1039G/+}$ mice.

Figure 4A:
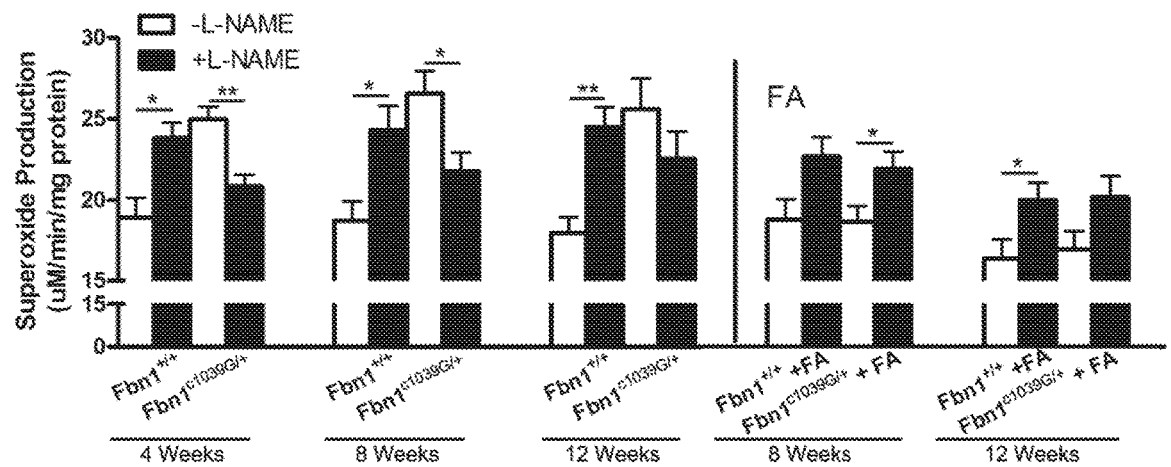
FIGS. 4A-4B. Folic acid diet prevents uncoupling of eNOS and preserves NO bioavailability in Fbn1$^{C1039G/+}$ mice. (4A) Total superoxide production in the presence or absence of L-NAME (NOS inhibitor) from aortic homogenates was determined by electron spin resonance (ESR). The eNOS uncoupling activity (L-NAME-inhibitable superoxide production) in Fbn1$^{C1039G/+}$ mice was completely attenuated by folic acid diet at both week 8 and week 12. n=5-7. (4B) NO bioavailability in aortic tissues was determined by ESR. Folic acid diet significantly preserved NO bioavailability in Fbn1$^{C1039G/+}$ mice at both week 8 and week 12. n=7-12. Data are presented as Mean±SEM, $*p<=0.05$, $**p<=0.01$.
Figure 4B:
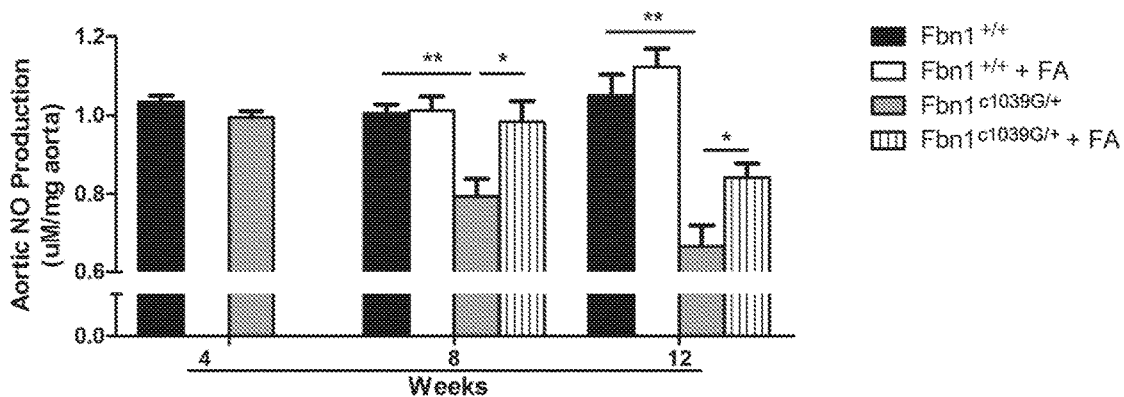

Consistent with the findings above that FA diet abolished aneurysm formation in $Fbn1^{C1039G/+}$ mice, and its remarkable effects in attenuating AAA formation in various novel and classical mouse models[19-22] FA diet was able to reduce superoxide production, improve NO bioavailability and abrogate eNOS uncoupling activity in $Fbn1^{C1039G/+}$ mice (FIG. 4).

Firstly, ESR was used to measure the aortic superoxide production with or without L-NAME, an inhibitor for NOS. If eNOS is functional and coupled, its inhibition by L-NAME will increase the measured superoxide due to lack of scavenging effects of NO on superoxide. However, if eNOS is dysfunctional and uncoupled, it produces superoxide and the inhibition with L-NAME will reduce measured superoxide. Hence, the difference between the superoxide values measured with and without L-NAME reflects the coupling/uncoupling status of eNOS. As is obvious in FIG. 4A, L-NAME-sensitive superoxide production, reflective of eNOS uncoupling activity, was significantly increased in $Fbn1^{C1039G/+}$ mice at 8 and 12 week old, which was completely attenuated by oral treatment with FA.

Since FA restored eNOS function, NO levels were next measured in isolated aortas from $Fbn1^{+/+}$ and $Fbn1^{C1039G/+}$ mice with/without oral FA treatment. The results, shown in FIG. 4B, demonstrate that NO bioavailability significantly decreased in the aortas of $Fbn1^{C1039G/+}$ mice compared with the $Fbn1^{+/+}$ mice at the age of 8 and 12 weeks, while FA markedly improved NO bioavailability in $Fbn1^{C1039G/+}$ mice.

These results indicate that FA prevented aneurysm formation via recoupling of eNOS to attenuate eNOS-derived superoxide production and improve NO bioavailability.

Folic acid restored tissue and circulating $H_4B$ levels in $Fbn1^{C1039G/+}$ animals.

Uncoupling of eNOS is caused by a reduced bioavailability of $H_4B$, which is the essential cofactor for proper eNOS coupling activity[21, 26, 28, 29, 41-43]. Therefore, to further examine the coupling state of eNOS, $H_4B$ bioavailability was determined by HPLC from the aortic and plasma samples of the $Fbn1^{+/+}$ and $Fbn1^{C1039G/+}$ animals at the age of 4, 8 and 12 weeks. The results in FIGS. 5A &5B indicate that the $H_4B$ levels in the aortas and plasma of $Fbn1^{C1039G/+}$ mice were significantly reduced compared to that of $Fbn1^{+/+}$ mice at the age of 4 weeks. After oral treatment of FA, the $H_4B$ levels in the aortas (FIG. 5A) and plasma (FIG. 5B) of both $Fbn1^{+/+}$ and $Fbn1^{C1039G/+}$ mice were substantially restored compared to chow diet feed mice, suggesting an improvement in the coupling state of eNOS with the FA treatment.

Figure 5A:
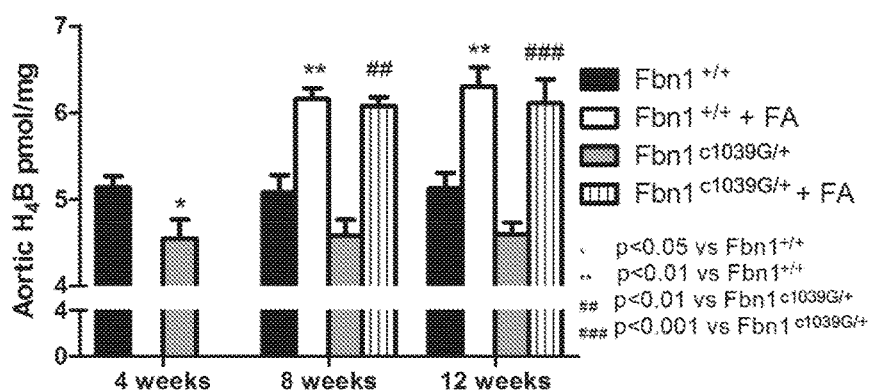
FIGS. 5A-5E. Folic acid diet increased tissue and circulating H$_4$B levels in Fbn1$^{+/+}$ and Fbn1$^{C1039G/+}$ animals. Aortic H$_4$B levels (5A) and plasma H$_4$B levels (5B) were determined by HPLC (n=5-7). Folic acid diet markedly increased tissue and circulating H$_4$B levels in both wild-type Fbn1$^{+/+}$ littermates and Fbn1$^{C1039G/+}$ mice. (5C) Correlation analysis of aortic H$_4$B and circulating H$_4$B levels indicating that circulating H$_4$B is accurately reflective of tissue H$_4$B levels, n=35. (5D) Correlation between aortic root diameter and aortic H$_4$B levels indicating that lower tissue H$_4$B levels are associated with bigger expansion of aortic roots, n=35. (5E) Correlation between aortic root diameter and plasma H$_4$B levels indicating that lower circulating H$_4$B levels are associated with bigger expansion of aortic roots, n=35. Data are presented as Mean±SEM.
Figure 5B:
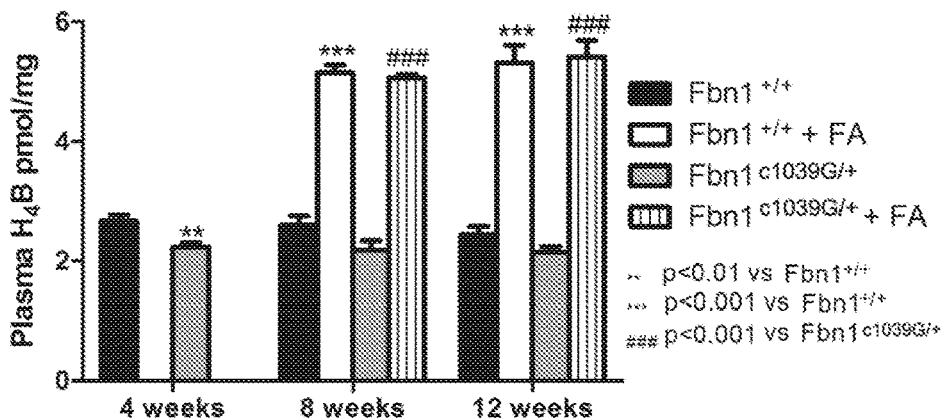
Figure 5C:
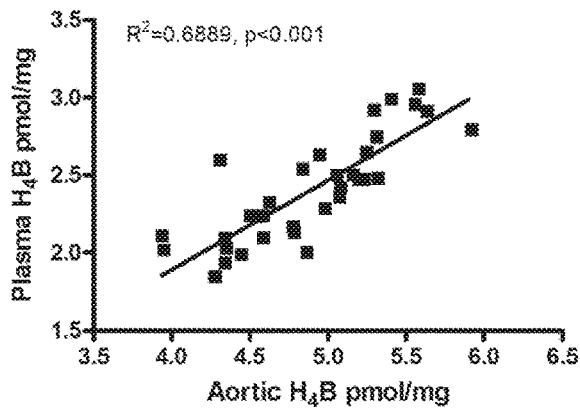
Figure 5D:
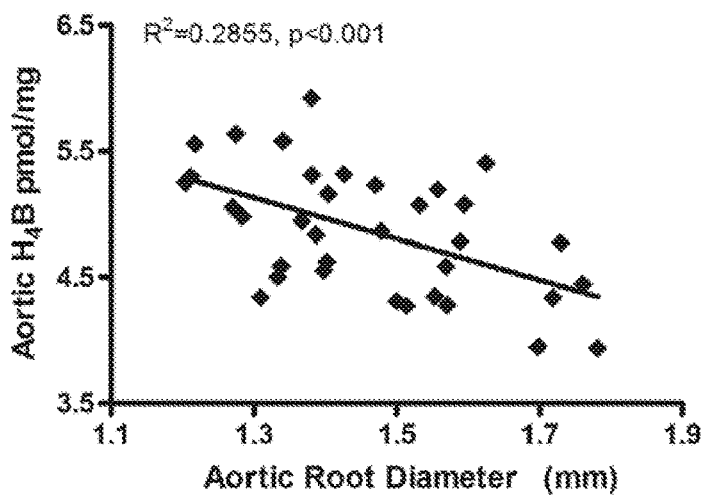
Figure 5E:
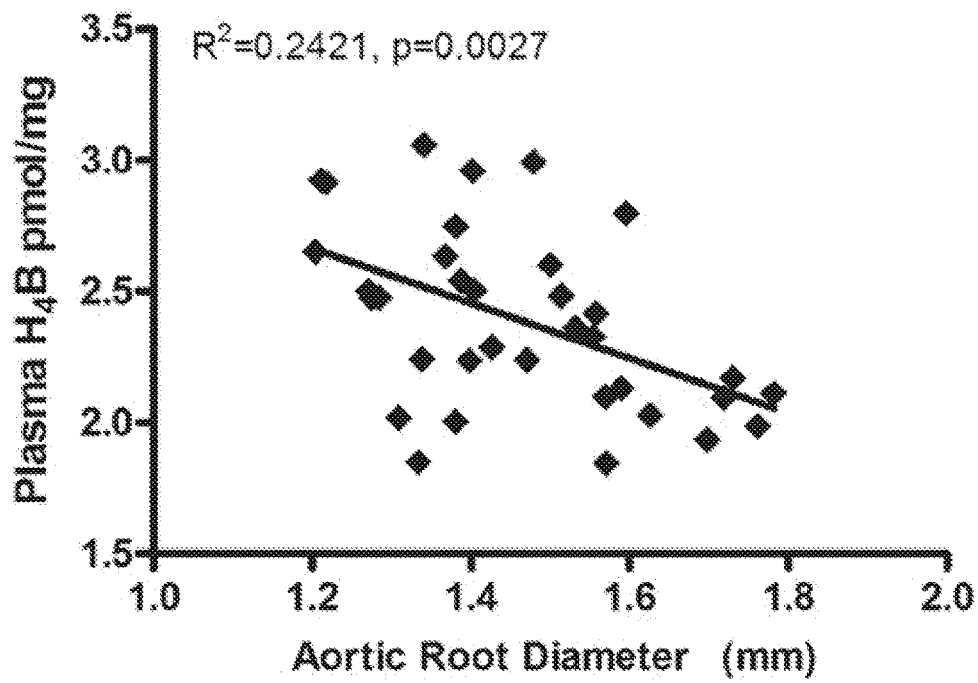

Recent study has showed that circulating $H_4B$ could be used as a novel biomarker for AAA[35]. Here, circulating levels of $H_4B$ were also detected in the plasma from $Fbn1^{C1039G/+}$ mice with or without FA treatment. As shown in FIG. 5B, the change of $H_4B$ levels in plasma was consistent with that in the aortas (FIG. 5A). Linear correlation between tissue and plasma $H_4B$ was calculated for the above data. FIG. 5C showed that circulating $H_4B$ levels correlated well with tissue $H_4B$ levels. Reduced $H_4B$ levels correlated well with bigger aortic root diameters in $Fbn1^{C1039G/+}$ animals (FIGS. 5D &5E).

These results indicate that $H_4B$ deficiency was involved in the eNOS uncoupling-dependent development of aneurysms, which was reversed by FA diet. In addition, circulating $H_4B$ levels may be used clinically as a powerful biomarker for the development and treatment response of TAA.

Oral folic acid treatment preserved DHFR expression and activity in aortas of Fbn1$^{C1039G/+}$ mice.

The above data show that restoration of eNOS coupling, which is tied to the bioavailability of H$_4$B, may be important in FA's protective effects against TAA in MFS animals. Previous studies have shown that FA treatment can recouple eNOS through the improvement of endothelial DHFR expression and activity in AAA, which is essential in salvaging H$_4$B[21, 22]. Here, endothelial DHFR activity and expression in Fbn1$^{C1039G/+}$ mice were examined to test whether DHFR is also improved during FA prevention of TAA in this model.

Figure 6A:
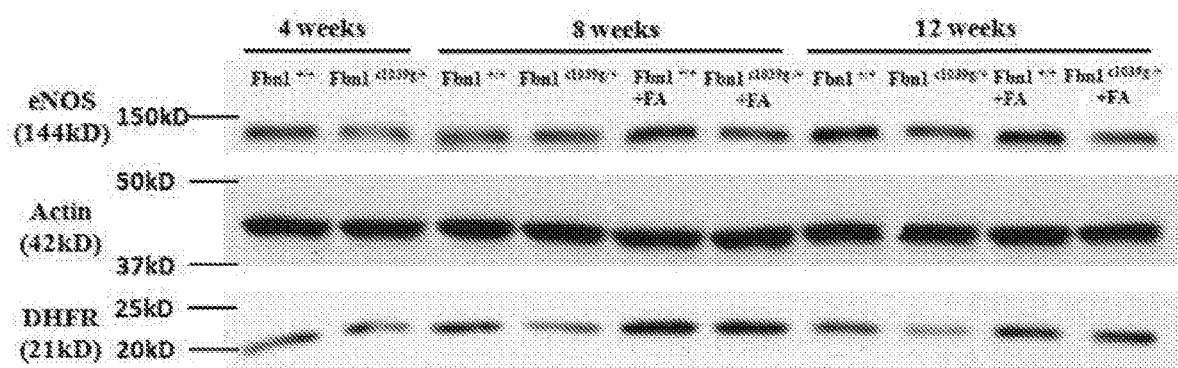
FIGS. 6A-6E. Folic acid diet prevents eNOS uncoupling via upregulation of DHFR protein expression and activity in Fbn1$^{c1039/+}$ mice. Endothelial cells (ECs) were isolated from aortas of Fbn1$^{+/+}$ and Fbn1$^{C1039G/+}$ mice. (6A) DHFR and eNOS expression levels were examined using Western blotting, with actin serving as internal control. (6B) Densitometric quantification of DHFR expression. (6C) Densitometric quantification of eNOS expression. DHFR activity was determined using HPLC from both isolated ECs (6D) and the denuded aortas (6E). Data are presented as Mean±SEM, n=5-8.
Figure 6B:
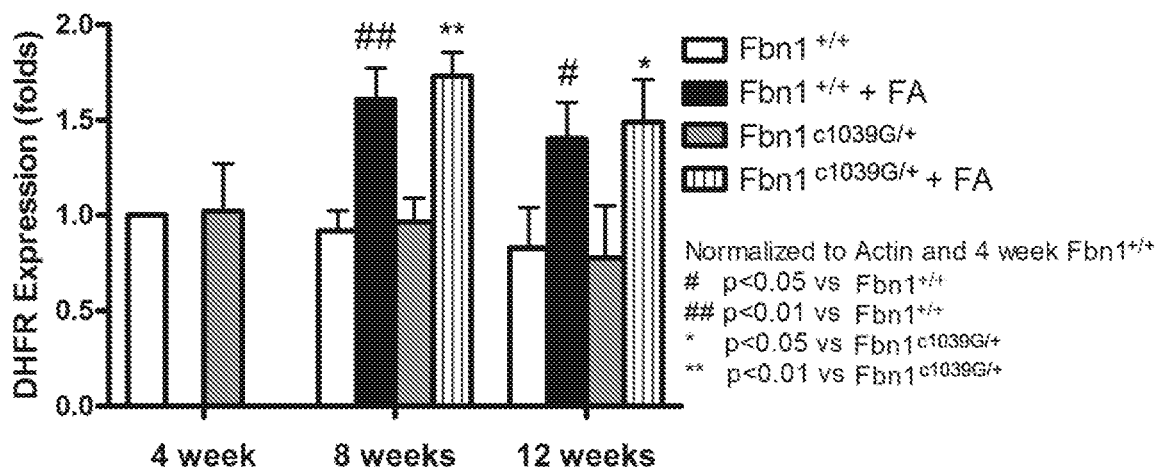
Figure 6C:
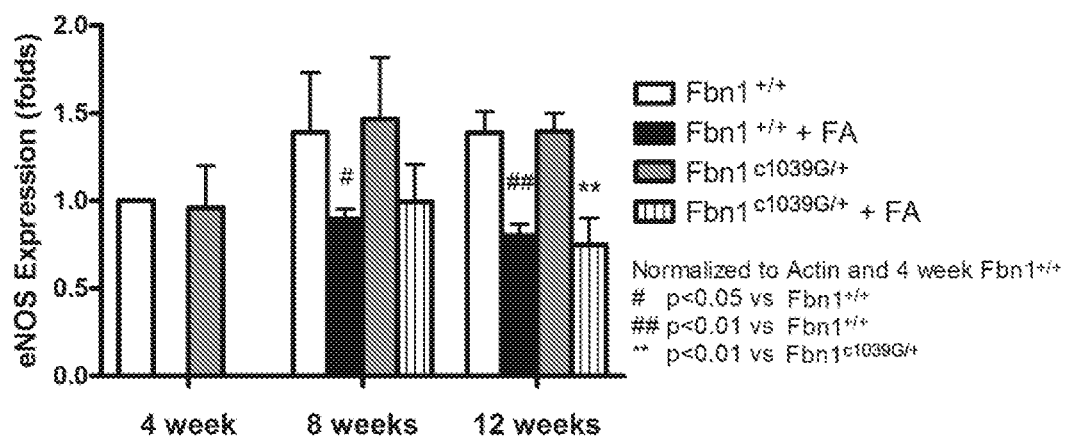
Figure 6D:
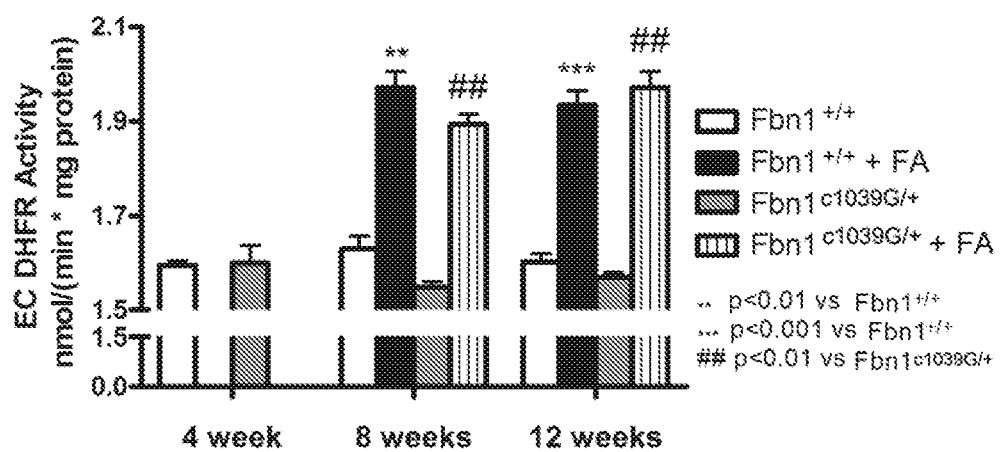
Figure 6E:
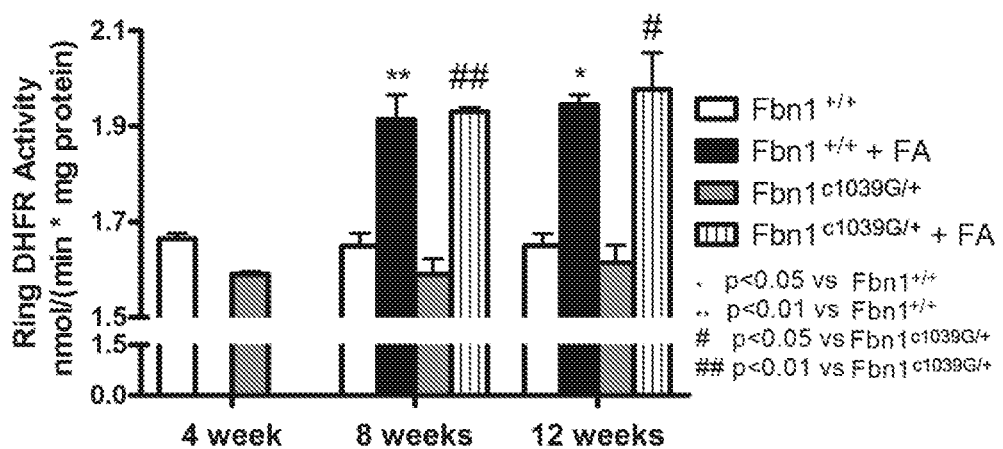

Endothelial cells (ECs) were isolated from freshly prepared aortas, Western blot was used to detect DHFR expression in aortic ECs and HPLC was performed to assess DHFR activity in the isolated ECs and the denuded aortas of the Fbn1$^{+/+}$ and Fbn1$^{C1039G/+}$ animals. FIG. 6A shows the representative Western blots for eNOS (144 kD), β-actin control (42 kD), and DHFR (21 kD). The expression of DHFR (FIG. 6B) rather than eNOS (FIG. 6C) was increased in both Fbn1$^{+/+}$ and Fbn1$^{C1039G/+}$ animals after FA treatment. As shown in FIGS. 6D & 6E, DHFR activity was measured via HPLC from both the isolated ECs (FIG. 6D) and the denuded aortas (FIG. 6E). DHFR activity in the isolated ECs and the denuded aortas of Fbn1$^{C1039G/+}$ and Fbn1l$^{+/+}$ mice were substantially increased by oral FA treatment.

These results clearly indicate that FA restoration of eNOS activity to attenuate TAA was accompanied by marked upregulation of DHFR expression and activity in Fbn1$^{C1039G/+}$ mice.

Figure 7A:
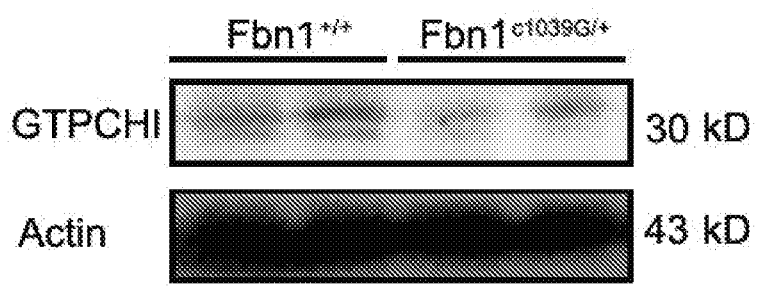
FIGS. 7A-7F. The protein expression levels of GTPCHI, TGFβ and NOX4 in Fbn1$^{C1039G/+}$ animals. (7A) Representative Western blot of GTPCHI protein expression in Fbn1$^{C1039G/+}$ mice compared to Fbn1$^{+/+}$ mice. (7B) Densitometric quantification of GTPCHI protein expression indicating down-regulated GTPCHI in Fbn1$^{C1039G/+}$ mice. (7C) Representative Western blot of inactive and mature TGFβ protein in aortas of Fbn1$^{C1039G/+}$ mice compared to Fbn1$^{+/+}$ mice. (7D) Densitometric quantification of inactive and mature TGFβ expression indicting upregulated mature TGFβ protein in Fbn1$^{C1039G/+}$ mice. (7E) Representative Western blot of NOX4 protein expression in Fbn1$^{C1039G/+}$ mice compared to Fbn1$^{+/+}$ mice. (7F) Densitometric quantification of NOX4 expression indicating upregulated NOX4 protein expression in Fbn1$^{C1039G/+}$ mice. Data are presented as Mean±SEM, n=4-9. $*p<0.05$.
Figure 7B:
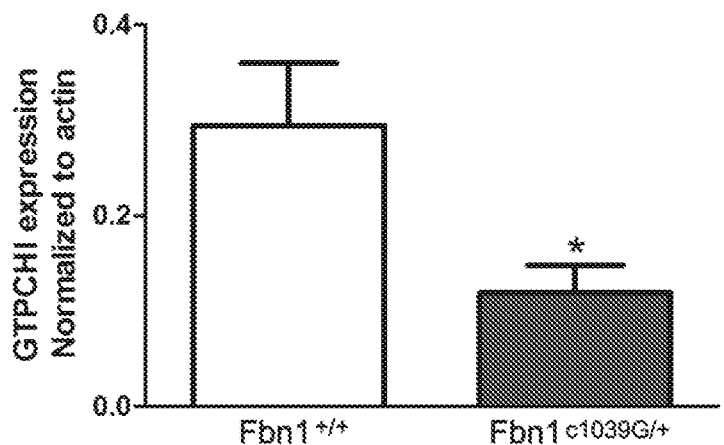

Of note, DHFR expression (FIGS. 6A &6B) was not changed at baseline despite a reduction in H$_4$B levels (FIGS. 5A &5B) in Fbn1$^{C1039G/+}$ mice compared to Fbn1$^{+/+}$ mice. Expression levels of the rate limiting H$_4$B synthetic enzyme GTPCHI (FIGS. 7A &7B) were examined in these animals and markedly reduced GTPCHI expression was found in Fbn1$^{C1039G/+}$ mice at baseline. Therefore, this regulation seems underlie reduced H$_4$B levels at baseline, while the beneficial effects of FA in improving H$_4$B bioavailability to recouple eNOS is mediated by substantial restoration of DHFR expression and activity.

Anti-TGFβ attenuates aortic root expansion by downregulation of NOX4 and recoupling of eNOS in Fbn1$^{C1039G/+}$ animals TGFβ signaling was found to play a crucial role in the development and maintenance of vasculature; mutations in TGFβ signaling pathway-related genes cause MFS[4]. Treatment with anti-TGFβ has been reported to prevent aortic aneurysm in the mouse model of MFS by modulating canonical TGFβ signaling pathway[14]. Noncanonical TGFβ signaling was also found to participate in aortic aneurysm progression in MFS mice[15]. Besides, NOX4 was found strongly induced by TGFβ during aneurysm formation and progression in Fbn1 MFS mice[24]. TGFβ also increased NOX4 expression and ROS production in primary culture of rat VSMCs in vitro[44]. NOX4 induces eNOS uncoupling in ECs under the conditions of AAA, cardiac ischemia/reperfusion (I/R) injury[45] and aging[46]. It is thus hypothesized that the Fbn1/TGFβ/NOX4 axis lies upstream of uncoupled eNOS in inducing TAA formation in MFS mice.

Figure 7C:
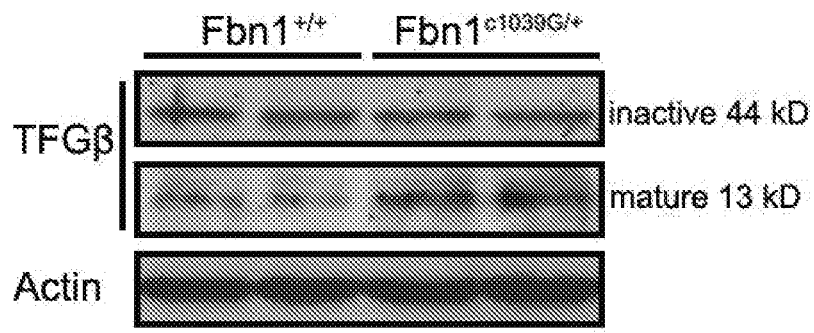
Figure 7D:
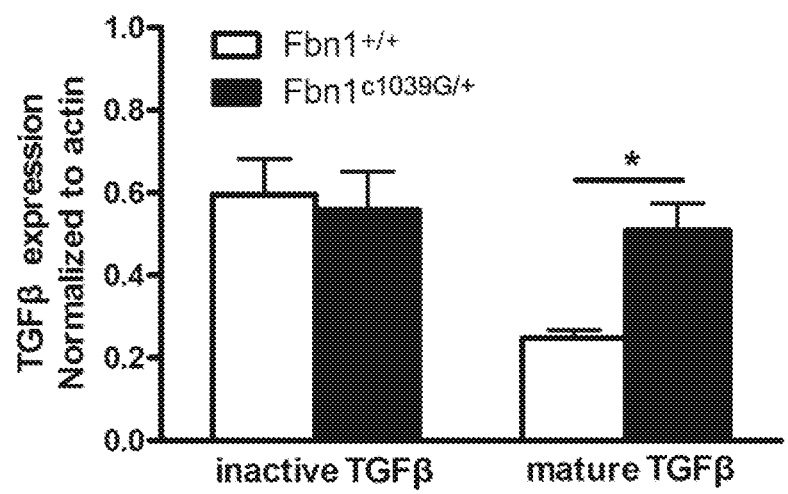
Figure 7E:
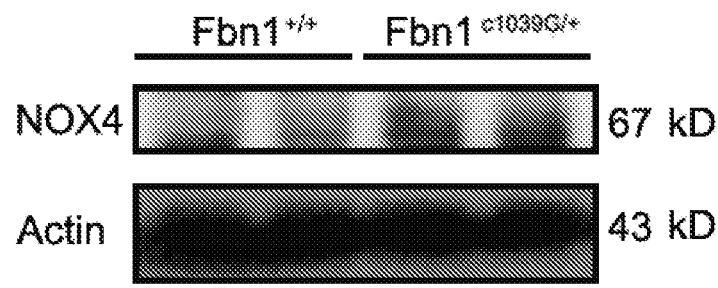
Figure 7F:
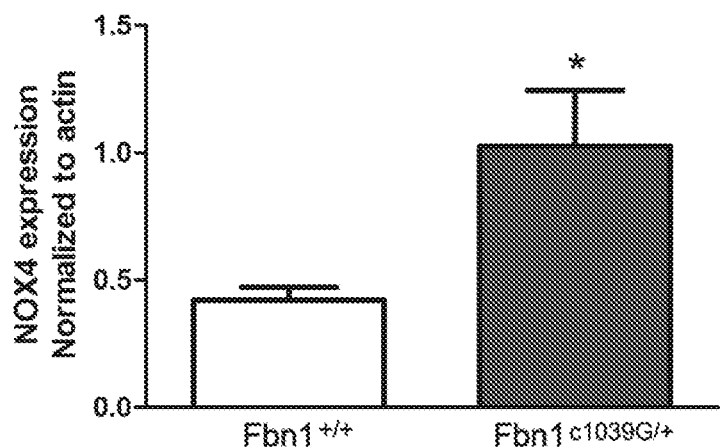

The results showed that the protein levels of mature TGFβ, rather than those of the inactive form of TGFβ, were significantly elevated in the aortas of Fbn1$^{C1039G/+}$ mice compared to Fbn1$^{+/+}$ mice (FIGS. 7C &7D). NOX4, downstream of mature TGFβ and known to uncouple eNOS, was also upregulated in Fbn1$^{C1039G/+}$ mice compared to Fbn1$^{+/+}$ mice (FIGS. 7E &7F).

Figure 8A:
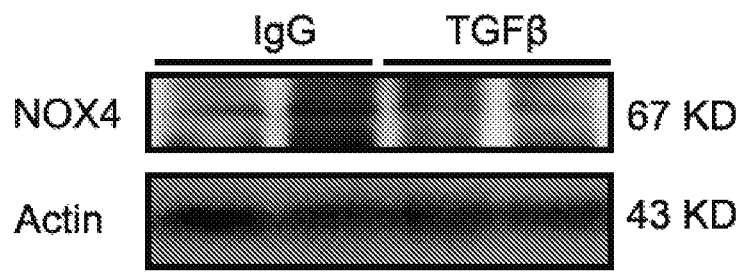
FIGS. 8A-8E. TGFβ blocking antibody attenuates aortic root expansion by NOX4 inhibition-dependent recoupling of eNOS in Fbn1$^{C1039G/+}$ mice. (8A) Representative Western blot of NOX4 expression in aortas of Fbn1$^{C1039G/+}$ mice treated with TGFβ blocking antibody. (8B) Densitometric quantification of NOX4 protein expression indicating inhibition by TGFβ blocking antibody. (8C) Aortic root diameter was decreased in Fbn1$^{C1039G/+}$ mice after injection of TGFβ blocking antibody for 3 and 4 weeks. (8D) Abdominal aorta diameter was yet changed by the 4 weeks injection of TGFβ blocking antibody in Fbn1$^{C1039G/+}$ mice. (8E) Total superoxide production in the presence or absence of L-NAME was determined by ESR in the aortic tissues of Fbn1$^{C1039G/+}$ mice after treatment with TGFβ blocking antibody for 4 weeks. The results indicate recoupling of eNOS by TGFβ blocking antibody. Data are presented as Mean±SEM, n=4-9. $*p<0.05$.
Figure 8B:
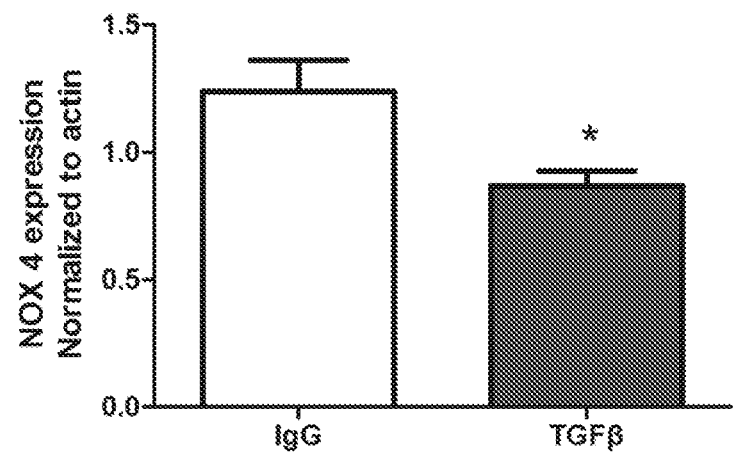
Figure 8C:
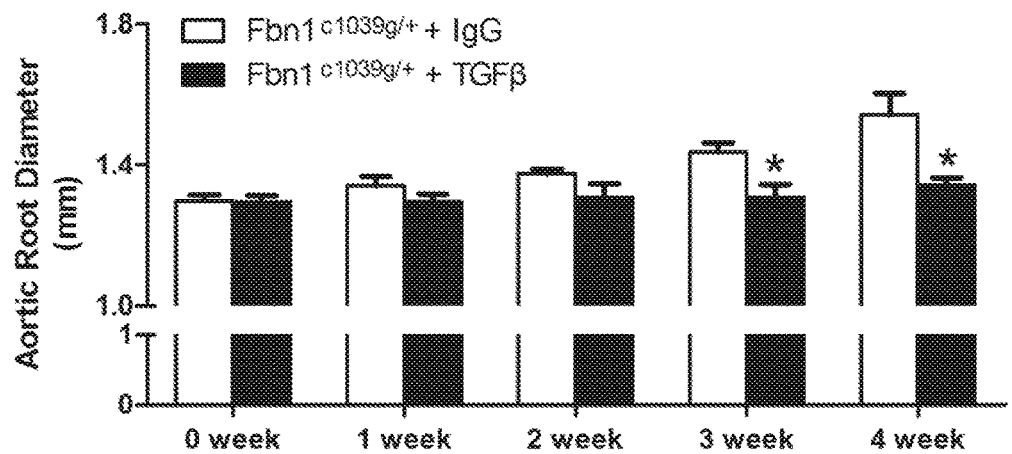
Figure 8D:
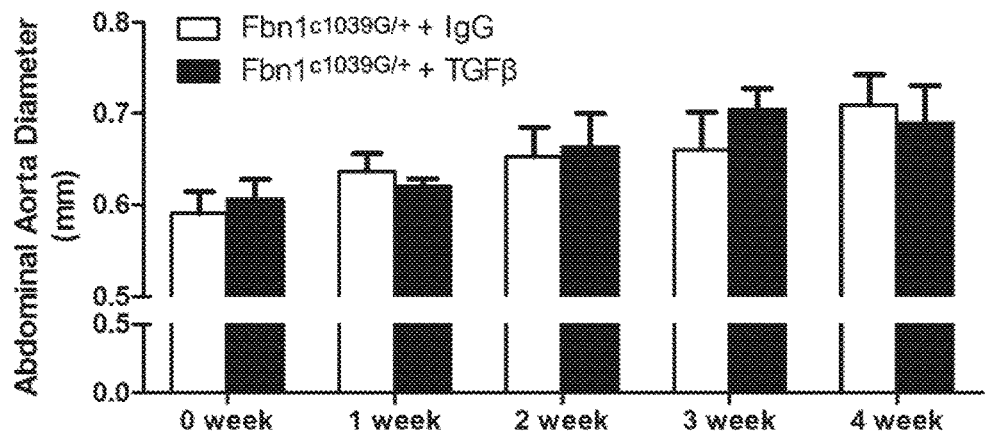
Figure 8E:
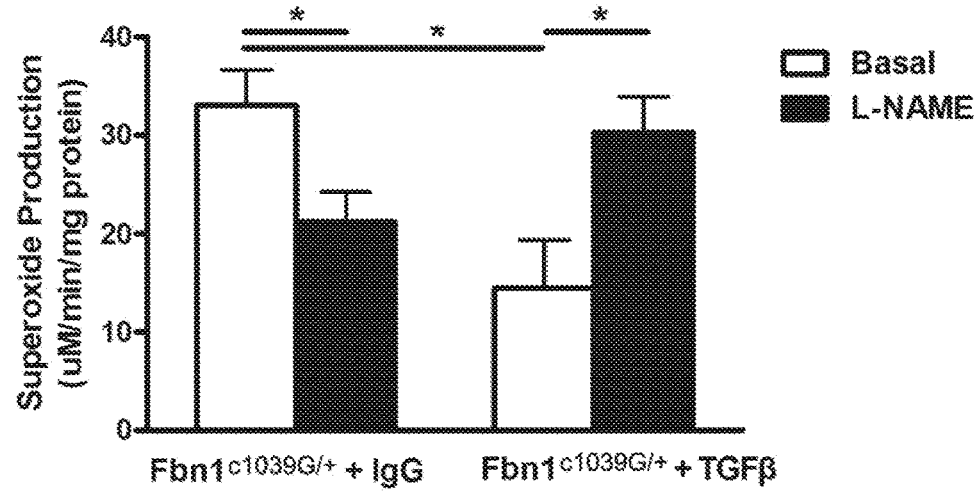

In addition, anti-TGFβ antibody decreased NOX4 expression compared to IgG injection in Fbn1$^{C1039G/+}$ mice (FIGS. 8A &8B). The aortic root diameter was reduced after injection of anti-TGFβ antibody for 3 and 4 weeks in Fbn1$^{C1039G/+}$ mice (FIG. 8C), while there was yet significant difference in abdominal aorta diameter between anti-TGFβ injection group and IgG injection group (FIG. 8D). The latter may be related to the relatively slower progression of AAA in Fbn1$^{C1039G/+}$ mice. eNOS uncoupling activity was determined after anti-TGFβ antibody injection in Fbn1$^{C1039G/+}$ mice. As shown in FIG. 8E, anti-TGFβ antibody treatment in vivo completely recoupled eNOS in Fbn1$^{C1039G/+}$.

Taken together, these data establish a novel TGFβ-NOX4-eNOS uncoupling axis that mediates TAA formation in Fbn1$^{C1039G/+}$ mice, and that recoupling of eNOS by FA diet or anti-TGFβ treatment prevents TAA via targeting components of this pathway.

DISCUSSION

Figure 9:
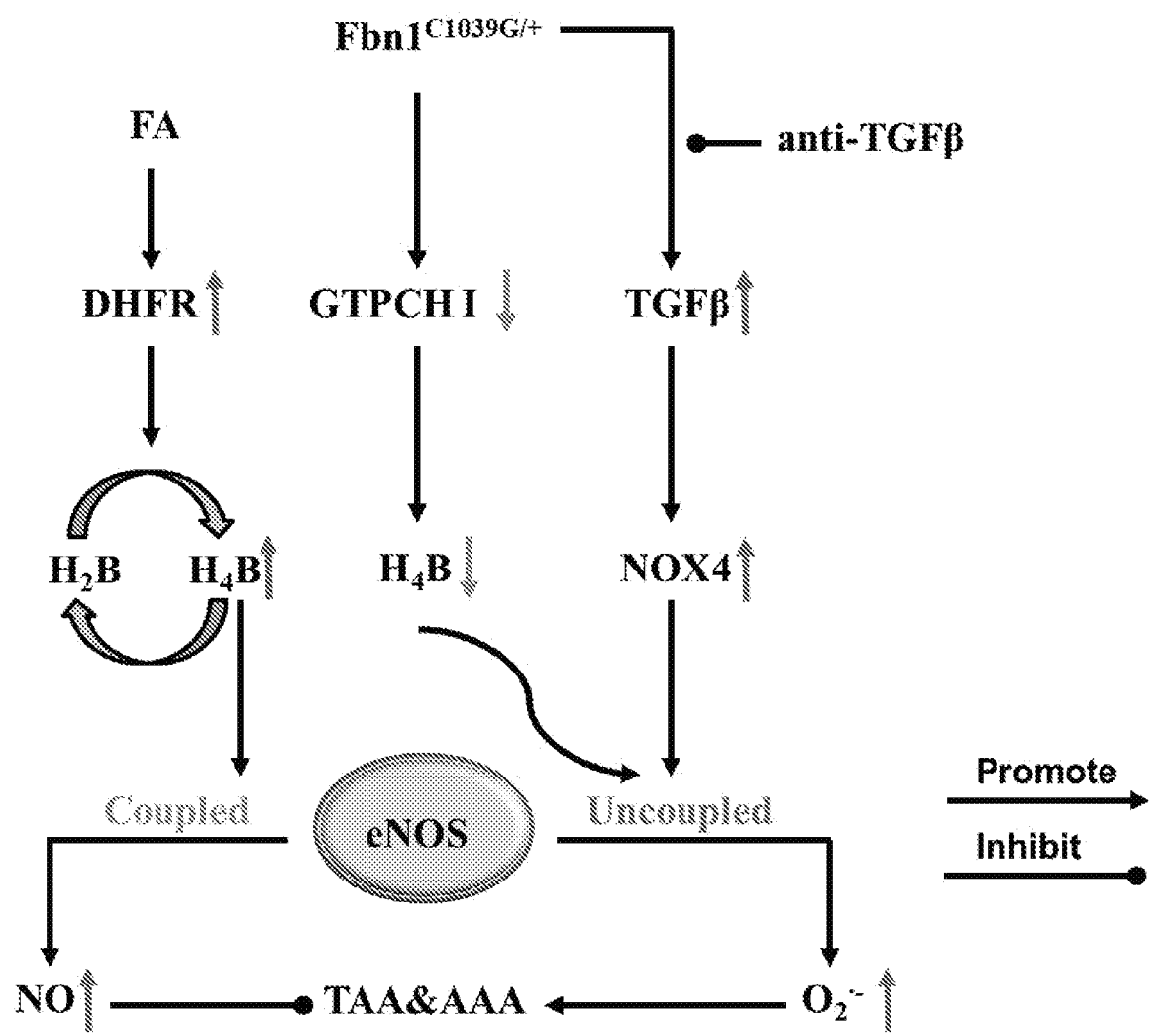
FIG. 9. Novel therapeutic effects of FA and TGFβ blocking antibody on TAA via attenuation of TGFβ/NOX4/eNOS uncoupling axis. FA substantially attenuates expansion of aortic roots and abdominal aortas via DHFR/H$_4$B/eNOS recoupling/NO pathway, while anti-TGFβ antibody decreases NOX4 expression to recouple eNOS in Fbn1/mice resulting in attenuation of TAA formation.

The most significant findings of the present study are the first demonstration of a causal role of eNOS uncoupling, and the therapeutic potential of eNOS recoupling by targeting Fbn1/TGFβ/NOX4 axis, in the formation of TAA in Fbn1$^{C1039G/+}$ MFS mice. FA substantially attenuates the diameters of aortic roots and abdominal aortas via DHFR/H$_4$B/eNOS recoupling/NO pathway in Fbn1$^{C1039G/+}$ mice (FIG. 9). Circulating H$_4$B is accurately reflective of aortic H$_4$B levels, and that aortic and circulating H$_4$B levels are negatively correlated with the diameters of aortic roots and abdominal aorta. The expression of mature TGFβ and its downstream effector NOX4 were elevated in Fbn1$^{C1039G/+}$ mice, while in vivo treatment with anti-TGFβantibody decreased NOX4 expression, recoupled eNOS and attenuated the diameters of aortic roots (FIG. 9). Therefore, oral FA treatment and anti-TGFβ that directed at recoupling eNOS may represent novel strategies for the treatment of TAA in Fbn1$^{C1039G/+}$ mice and other types of TAA.

Oxidative stress has been proven to play a vital role in the pathogenesis of aortic aneurysms, particularly for AAA.[17-22, 47] Previous work has elucidated that FA completely or largely attenuated AAA formation via recoupling of eNOS[21, 22]. This example examined whether oxidative stress and uncoupled eNOS are responsible for TAA formation in Fbn1$^{C1039G/+}$ mice, and makes a thorough inquiry if FA could be used a potential oral medicine for TAA treatment in Fbn1$^{C1039G/+}$ mice. Previous studies reveal that there are positive correlations between oxidative stress and severity of TAA[23, 48-50]. An excessive production of ROS has been implicated as a pathogenetic mechanism in aortic aneurysm and other manifestations occurring in MFS[23, 51, 52]. Here, eNOS was found to be uncoupled in TAA of Fbn1$^{C1039G/+}$ mice to produce superoxide (FIG. 4A), and this is the first evidence that eNOS uncoupling serves as a primary source of ROS for TAA formation (FIG. 3A). Surprisingly, these results are similar to what was found in AAA[19-22, 32], and ischemia/reperfusion (I/R) injury of the heart[45, 53, 54]. Since oral administration of FA could restore eNOS coupling activity to prevent AAA formation in novel and classical models of AAA including Ang II infused hph-1 mice and Ang II-infused apoE null mice[21, 22, 26], whether FA is equally robust in recoupling of eNOS to attenuate TAA formation in Fbn1$^{C1039G/+}$ mice was investigated. The results show that FA completely restores eNOS coupling activity to improve NO bioavailability, resulting in abrogated expansion of aortic roots and abdominal aortas in Fbn1$^{C1039G/+}$ mice. These data demonstrate that FA diet could represent a novel therapeutic strategy for TAA via restoration of eNOS coupling activity.

H$_4$B deficiency switches eNOS from the coupled to the uncoupled state[21, 26, 23, 29, 41-43]. The present study found that aortic and circulating H$_4$B levels were substantially reduced in Fbn1$^{C1039G/+}$ (FIGS. 5A & 5B), which was accompanied by eNOS uncoupling activity. The results further showed that oral administration of FA restores H$_4$B bioavailability both in the tissues and plasma (FIGS. 5A & 5B), which was associated with abrogated eNOS uncoupling activity and prevention of TAA formation in Fbn1$^{C1039G/+}$ mice. Of note, aortic and plasma H$_4$B levels were quantitatively correlated with sizes of aortic roots, with lower H$_4$B levels corresponding to bigger aortic root dimension. Therefore, the present data for the first time demonstrate a biomarker role of circulating H$_4$B for the formation of TAA in Fbn1$^{C1039G/+}$ mice.

Much work over the past decade has established an essential role of H$_4$B salvage enzyme DHFR in regulating H$_4$B bioavailability, eNOS coupling/uncoupling activity and vascular pathogenesis when deficient[19, 22, 26, 28, 290, 36, 55, 56]. DHFR deficiency induces a reduction in H$_4$B bioavailability and consequent eNOS uncoupling to result in development of cardiovascular diseases, including hypertension, aortic aneurysms, diabetic vascular complications, I/R injury and heart failure[19-22, 26, 30, 32, 33, 36, 57]. The expression of DHFR and the activity of DHFR in ECs of the aorta were all improved in Fbn1$^{C1039G/+}$ mice after FA treatment, indicating a novel observation of DHFR-dependent attenuation of TAA. The similar results have been reported in AAA[19-22]. Thus, FA treatment can recouple eNOS through the improvement of endothelial DHFR function in both AAA and TAA. It's worth noting that the expression and activity of DHFR in ECs were not decreased at baseline, while a reduction in GTPCHI protein expression seems to account for basal H$_4$B deficiency in Fbn1$^{C1039G/+}$ animals. Whether this loss in GTPCHI is directly downstream of Fbn1 deficiency needs further investigation.

Mutation of fibrillin-1 leads to uncontrolled release of TGFβ and activation of the TGFβ pathway[7, 58, 59]. NOX4 expression level is strongly induced by TGFβ in aneurysm formation and progression in the murine model of MFS[24]. And the diameter of aortic root is abrogated in Fbn1$^{C1039G/+}$ mice after NOX4 knockout[24]. However, the intermediate role of NOX4 in aneurysm formation in MFS has not been fully elucidated. This example presents novel findings that the mature form of TGFβ, rather than its inactive form, was elevated in Fbn1$^{C1039G/+}$ mice compared to WT littermates (FIGS. 7C & 7D). NOX4 protein expression was also increased (FIG. 7C) and eNOS was uncoupled (FIG. 4A), Treatment with anti-TGFβ antibody decreased total superoxide production and recoupled eNOS (FIG. 8E) by reducing NOX4 expression (FIG. 8A), which resulted in attenuated aortic root expansion (FIG. 8C) in Fbn1$^{C1039G/+}$ mice. These results indicated that NOX4 is downstream of TGFβ signaling in mediating TAA formation in Fbn1$^{C1039G/+}$ mice. Similarly, expression of NOX4 was found upregulated in human AAA segments and in Ang II-treated ApoE$^{-/-}$ mouse aortas[60]. NOX4 is also significantly upregulated by homocysteine (Hcy)-aggravated AAA formation in ApoE$^{-/-}$ mice, and NOX4 siRNA diminished Hcy-induced adventitial fibroblasts activation[61]. Knockout of NOX4 reduces incidence of AAA in Ang II-treated hph-1 mice via recoupling of eNOS[19]. In cardiac ischemia/reperfusion (I/R) injured mice, NOX4 RNAi decreased infarct size via recoupling of eNOS[45]. NOX4 was also found to mediate eNOS uncoupling in vitro. In ECs, NOX4 primarily contributes to eNOS uncoupling during the aging process[46]. In glomerular mesangial cells, inhibition of NOX4 abrogates eNOS uncoupling triggered by high glucose or Ang II, demonstrating that NOX4 activation leads to eNOS uncoupling[62, 63]. Take together, these findings establish that NOX4/eNOS uncoupling lies downstream of TGFβ to mediate TAA formation in Fbn1$^{C1039G/+}$ mice.

In summary, the data elucidate that theTGFβ/NOX4/eNOS uncoupling axis is innovatively responsible for TAA formation in MFS mice, targeting of which with FA diet (via DHFR/H$_4$B/eNOS recoupling/NO pathway) or in vivo anti-TGFβ antibody treatment (via inhibition of NOX4) abrogates TAA formation by recoupling of eNOS. These findings provide novel targeted therapeutics for the treatment or prevention of TAA in humans.

REFERENCES

1. Lindsay M E, Dietz H C. *Nature* 2011; 473:308-316.
2. Benjamin E J, et al. *Circulation* 2019; 139:e56-e66.
3. Isselbacher E M, et al. *Circulation* 2016; 133:2516-252B.
4. Gillis E, et al. *Circulation research* 2013; 113:327-340.
5. Davis F M, et al. *Arteriosclerosis, thrombosis, and vascular biology* 2019; 39:e83-e90.
6. Guo J, et al. *Scientific reports* 2015; 5:13115.
7. Isogai Z, et al. *The Journal of biological chemistry* 2003; 278:2750-2757.
8. Dietz H C, et al. *Nature* 1991; 352:337-339.
9. Sherratt M J, et al. *Micron* 2001; 32:185-200.
10. Braverman A C, et al. *Circulation* 2015; 132:e303-309.
11. Mc K V. *Circulation* 1955; 11:321-342.
12. Daugherty A, et al. *Journal of the American Heart Association* 2017:6.
13. Lu H, Daugherty A. *Arteriosclerosis, thrombosis, and vascular biology* 2017; 37:e59-e65.
14. Habashi J P, et al. *Science* 2006; 312:117-121.
15. Holm T M, et al. *Science* 2011; 332:358-361.
16. Chen X, et al. *PloS one* 2016; 11:e0153811.
17. Thomas M, et al. *Circulation* 2006; 114:404-413.
18. Gavrila D, et al. *Arteriosclerosis, thrombosis, and vascular biology* 2005; 25:1671-1677.
19. Siu K L, et al. *Redox biology* 2017; 11:118-125.
20. Miao X N, Siu K L, Cai H. *Journal of molecular and cellular cardiology* 2015; 87:152-159.
21. Gao L, et al. *Hypertension* 2012; 59:158-166.
22. Siu K L, et al. *PloS one* 2014; 9:e88899.
23. Ejiri J, et al. *Cardiovascular research* 2003; 59:988-996.
24. Jimenez-Altayo F, et al. *Free radical biology & medicine* 2018; 118:44-58.
25. Onetti Y, et al. *American journal of physiology Heart and circulatory physiology* 2016; 310:H1081-1090.
26. Gao L, et al. *Journal of molecular and cellular cardiology* 2009; 47:752-760.
27. Youn J Y, et al. *Molecular endocrinology* 2015; 29:1123-1133.
28. Chalupsky K, et al. *Proceedings of the National Academy of Sciences of the United States of America* 2005; 102:9056-9061.
29. Oak J H, et al *Diabetes* 2007; 56:118-126.
30. Youn J Y, et al. *Diabetologia* 2012; 55:2069-2079.
31. Youn J Y, et al. *Diabetes* 2014:63:2344-2355.
32. Li Q, et al. *Redox biology* 2019:24:101185.
33. Li H, et al. *Hypertension* 2019; 73:179-189.

34. Youn J Y, et al. *Circulation research* 2009; 104:50-59.
35. Siu K L, Cai H. *American journal of physiology Heart and circulatory physiology* 2014; 307:1H1559-1564.
36. Crabtree M J, et al. *The Journal of biological chemistry* 2009; 284:28128-28136.
37. Chuaiphichai S, et al. *British journal of pharmacology* 2017; 174:657-671.
38. Alp N J, et al. *The Journal of clinical investigation* 2003; 112:725-735.
39. Cai S, et al. *Cardiovascular research* 2002; 55:838-849.
40. Manlove L S, et al. *Journal of immunology* 2015; 195: 4028-4037.
41. Vasquez-Vivar J, et al. *Proceedings of the National Academy of Sciences of the United States of America* 1998; 95:9220-9225.
42. Wever R I M, et al. *Biochemical and biophysical research communications* 1997; 237:340-344.
43. Xia Y, et al. *The Journal of biological chemistry* 1998; 273:25804-25808.
44. Liu X H, et al. *Free radical biology & medicine* 2016; 94:174-184.
45. Siu K L, et al. *Journal of molecular and cellular cardiology* 2015; 78:174-185.
46. Lee H Y, et al. *Free radical biology & medicine* 2017; 113:26-35.
47. Miller F J, Jr., et al. *Arteriosclerosis, thrombosis, and vascular biology* 2002; 22:560-565.
48. Branchetti E, et al. *Cardiovascular research* 2013; 100:316-324.
49. Liao M, et al. *The Journal of thoracic and cardiovascular surgery* 2008; 136:65-72, 72 e61-63.
50. Fiorillo C, et al. *International Journal of Cardiology* 2010; 145:544-546.
51. Phillippi J A, et al. *Circulation* 2009; 119:2498-2506.
52. Tabakoglu E, et al. *Mediators of inflammation* 2004; 13:209-210.
53. Hallstrom S, et al. *Cardiovascular research* 2008; 77:506-514.
54. Mendez-Carmona N, et al. *The Journal of heart and lung transplantation: the official publication of the International Society for Heart Transplantation* 2019.
55. Thony B, et al. *The Biochemical journal* 2000; 347 Pt 1:1-16.
56. Michel T. NO way to relax: the complexities of coupling nitric oxide synthase pathways in the heart. *Circulation* 2010; 121:484-486.
57. Cario H, et al. *American Journal of human genetics* 2011; 88:226-231.
58. Dallas S L, et al. *The Journal of cell biology* 1995; 131:539-549.
59. Dallas S L, et al. *Journal of bone and mineral research: the official journal of the American Society for Bone and Mineral Research* 2000; 15:68-81.
60. Lu V A, et al. *Arteriosclerosis, thrombosis, and vascular biology* 2016; 36:2176-2190.
61. Liu Z, et al. *Circulation research* 2012; 111:1261-1273.
62. Eid A A, et al. *Molecular and cellular biology* 2013; 33:3439-3460.
63. Lee D Y, et al. *The Journal of biological chemistry* 2013; 288:28668-28686.

Throughout this application various publications are referenced. The disclosures of these publications in their entireties are hereby incorporated by reference into this application in order to describe more fully the state of the art to which this invention pertains.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A method for treating thoracic aortic aneurysm (TAA) in a subject having TAA, the method comprising:
    (a) measuring, in a test sample of serum, plasma or whole blood from the subject, the amount of tetrahydrobiopterin ($H_4B$) present in the test sample; wherein a decrease is detected in the measured amount of $H_4B$ present in the test sample relative to a standard amount of $H_4B$; and
    (b) treating the subject with oral administration of folic acid or dihydrofolate reductase (DHFR) gene therapy.

2. The method of claim 1, wherein the decrease is a 30% decrease in the amount of $H_4B$ present in the test sample compared to the standard.

3. The method of claim 1, wherein the decrease is a 40% decrease in the amount of $H_4B$ present in the test sample compared to the standard.

4. The method of claim 1, wherein the decrease is a 50% decrease in the amount of $H_4B$ present in the test sample compared to the standard.

5. The method of claim 1, wherein the measuring comprises an immunoassay or a chemiluminescence assay.

6. The method of claim 1, wherein the measuring comprises high performance liquid chromatography (HPLC).

7. The method of claim 1, wherein the treating comprises oral administration of folic acid.

8. The method of claim 1, wherein the decrease is a 20% decrease in the amount of $H_4B$ present in the test sample compared to the standard.

9. The method of claim 1, wherein the sample is plasma.

10. The method of claim 1, further comprising measuring, in a second test sample of serum, plasma or whole blood obtained from the subject at a second time point, the amount of $H_4B$ present in the second test sample; wherein treatment with folic acid therapy is administered to the subject prior to the second time point.

11. The method of claim 10, wherein a 20% increase is measured in the amount of $H_4B$ present in the second test sample compared to the amount of $H_4B$ measuring in step (a).

12. The method of claim 10, further comprising prescribing a modified treatment for TAA to the subject whose $H_4B$ is decreased in the second test sample compared to the amount measured in step (a).

13. The method of claim 1, further comprising prescribing a modified treatment for TAA to the subject whose $H_4B$ is insufficiently increased in the second test sample compared to the amount measured in step (a).

14. The method of claim 1, wherein the decrease is a 60% decrease in the amount of $H_4B$ present in the test sample compared to the standard.

15. The method of claim 1, wherein the decrease is a 70% decrease in the amount of $H_4B$ present in the test sample compared to the standard.

16. The method of claim 1, wherein the decrease is a 80% decrease in the amount of $H_4B$ present in the test sample compared to the standard.

* * * * *